United States Patent
Kawakami et al.

(10) Patent No.: US 10,023,883 B2
(45) Date of Patent: Jul. 17, 2018

(54) METHOD FOR TREATING SUGAR SOLUTION, HYDROGENATED SUGAR SOLUTION, METHOD FOR PRODUCING ORGANIC COMPOUND, AND METHOD FOR CULTURING MICROORGANISMS

(71) Applicant: MITSUBISHI CHEMICAL CORPORATION, Chiyoda-ku (JP)

(72) Inventors: Kiminori Kawakami, Yokohama (JP); Takanao Matsumoto, Yokohama (JP); Shigeki Nitta, Yokohama (JP); Syuuichi Yunomura, Yokohama (JP); Masaru Utsunomiya, Chiyoda-ku (JP); Yuusuke Izawa, Yokkaichi (JP)

(73) Assignee: Mitsubishi Chemical Corporation, Chiyoda-ku (JP)

( * ) Notice: Subject to any disclaimer, the term of this patent is extended or adjusted under 35 U.S.C. 154(b) by 0 days.

(21) Appl. No.: 14/984,252

(22) Filed: Dec. 30, 2015

(65) Prior Publication Data

US 2016/0177346 A1 Jun. 23, 2016

Related U.S. Application Data

(63) Continuation of application No. PCT/JP2014/067719, filed on Jul. 2, 2014.

(30) Foreign Application Priority Data

Jul. 2, 2013 (JP) .................. 2013-139141

(51) Int. Cl.
*C12P 7/46* (2006.01)
*C12P 7/06* (2006.01)
*C12P 7/18* (2006.01)
*C12N 1/14* (2006.01)
*C12N 1/16* (2006.01)
*C12N 1/20* (2006.01)

(52) U.S. Cl.
CPC .................. *C12P 7/46* (2013.01); *C12N 1/14* (2013.01); *C12N 1/16* (2013.01); *C12N 1/20* (2013.01); *C12P 7/06* (2013.01); *C12P 7/18* (2013.01); *Y02E 50/17* (2013.01)

(58) Field of Classification Search
None
See application file for complete search history.

(56) References Cited

U.S. PATENT DOCUMENTS

| | | | |
|---|---|---|---|
| 5,096,820 A | 3/1992 | Leleu et al. | |
| 5,436,329 A * | 7/1995 | Caboche | A23G 3/346 127/29 |
| 5,843,760 A * | 12/1998 | Zhang | C12N 9/10 435/161 |
| 2005/0192436 A1 | 9/2005 | Komiya | |
| 2011/0250637 A1 | 10/2011 | Kurihara et al. | |
| 2013/0273608 A1 | 10/2013 | Hanakawa et al. | |

FOREIGN PATENT DOCUMENTS

| | | |
|---|---|---|
| JP | 3-195491 | 8/1991 |
| JP | 6-14741 | 1/1994 |
| JP | 11-506934 | 6/1999 |
| JP | 11-206325 A | 8/1999 |
| JP | 2001-95594 | 4/2001 |
| JP | 2005-270056 | 10/2005 |
| JP | 2007-151612 A | 6/2007 |
| JP | 2010-284120 | 12/2010 |
| JP | 2011-78327 | 4/2011 |
| WO | WO 96/40970 A1 | 12/1996 |
| WO | WO 02/083701 A1 | 10/2002 |
| WO | WO 2009/110374 A1 | 9/2009 |
| WO | WO 2010/067785 A1 | 6/2010 |
| WO | WO 2011/080129 A2 | 7/2011 |

OTHER PUBLICATIONS

International Search Report dated Sep. 22, 2014 in PCT/JP2014/067719 filed Jul. 2, 2014 (with English translation).
Written Opinion dated Sep. 22, 2014 in PCT/JP2014/067719 filed Jul. 2, 2014.
R. R. M. Zautsen, et al., "Liquid-Liquid Extraction of Fermentation Inhibiting Compounds in Lignocellulose Hydrolysate", Biotechnology and Bioengineering, vol. 102, (5), 2009, 7 pgs.
Adnan Cavka, et al., "Effect of Sulfur Oxyanions on Lignocellulose-Derived Fermentation Inhibitors", Biotechnology and Bioengineering, vol. 108, (11), 2011, 10 pgs.
I.S. Maddox, et al., "Production of n-Butanol by Fermentation of Wood Hydrolysate", Biotechnology Letters, vol. 5, (3), 1983, 4 pgs.
Office Action dated Feb. 6, 2018 in Japanese Patent Application No. 2015-525268 (with unedited computer generated English translation), 6 pages.
M.W. Kearsley, "The control of hygroscopicity, browning and fermentation in glucose syrups", J. Fd Technol, vol. 13, 1978, pp. 339-348.

* cited by examiner

*Primary Examiner* — Christian Fronda
(74) *Attorney, Agent, or Firm* — Oblon, McClelland, Maier & Neustadt, L.L.P.

(57) ABSTRACT

Provided are a method for treating a saccharide solution, which comprises subjecting a saccharide solution containing at least one selected from the group consisting of a carbonyl compound and an unsaturated alcohol other than a saccharide to hydrogenation reaction to hydrogenate the carbonyl compound and/or the unsaturated alcohol contained in the saccharide solution, a hydrogenated saccharide solution obtained by treating with the treatment method, and a method for producing an organic compound having a process of obtaining the organic compound by acting a microorganism having an organic material producing ability on an organic raw material containing the hydrogenated saccharide solution.

13 Claims, 1 Drawing Sheet

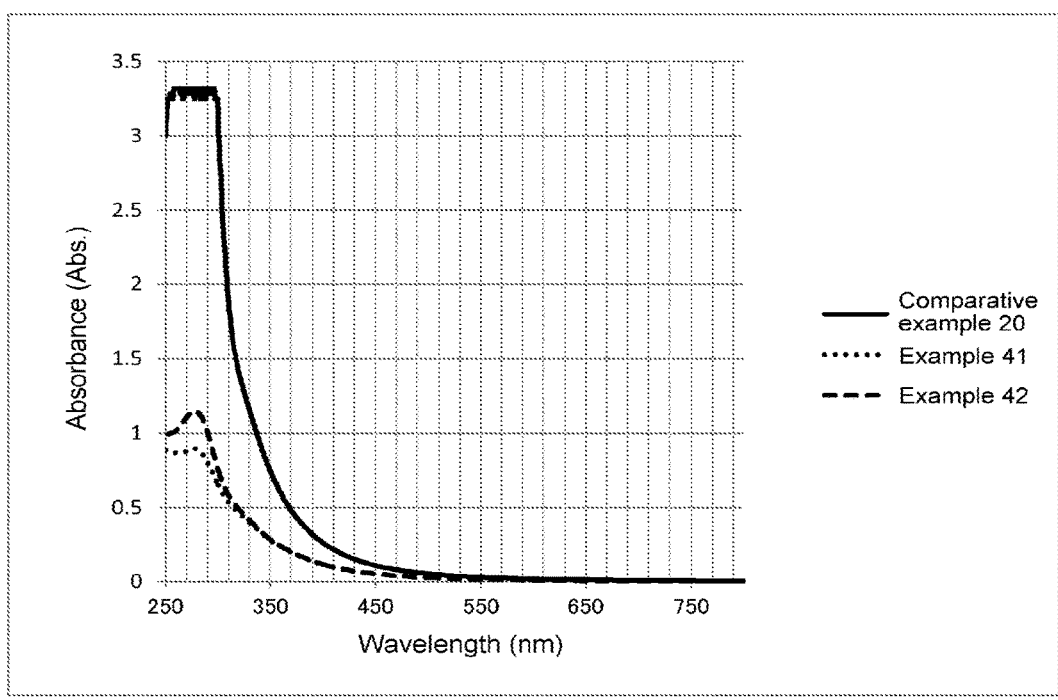

METHOD FOR TREATING SUGAR SOLUTION, HYDROGENATED SUGAR SOLUTION, METHOD FOR PRODUCING ORGANIC COMPOUND, AND METHOD FOR CULTURING MICROORGANISMS

TECHNICAL FIELD

The present invention relates to a method for treating a saccharide solution, and a hydrogenated saccharide solution obtained by the treatment. It also relates to a method for producing an organic compound using the hydrogenated saccharide solution and a culturing method of microorganism.

BACKGROUND ART

A fermentation production process and a chemical conversion process of an organic compound using a saccharide as a raw material have widely been utilized, and a product obtained by the above-mentioned respective processes has been utilized as a raw material for various industries.

At present, as a saccharide to be used as a raw material for these fermentation production processes and chemical conversion processes, those derived from edible raw materials such as saccharide cane, starch, saccharide beets, corn, potato, cassava, saccharide maple, etc., have been mentioned.

However, when these saccharides derived from the edible raw materials are used as a raw material of the above-mentioned processes, there are concerns that price rise of edible raw materials due to expecting population growth in the world and short supply of edible raw materials due to bad weather or climate change. In addition, at the time of food shortages, there is also concern about criticism such as ethical for utilizing edible raw materials for industrial raw materials to compete with an edible use. Thus, it is the problem in the future to construct a process for efficiently producing a liquid (saccharide solution) containing a saccharide inedible raw materials from a saccharide with lower purity containing impurities, or a process which can efficiently convert the obtained saccharide solution to an industrial raw material as a fermentation production raw material or a chemical conversion raw material.

As a method for obtaining a saccharide solution from inedible raw materials, there are mentioned a method in which cellulose or hemicellulose in inedible raw materials is hydrolyzed by using conc. sulfuric acid to a monosaccharide such as a hexose represented by glucose, or a pentose represented by xylose (Patent Document 1), a method in which after subjecting to a pre-treatment to improve reactivity of inedible raw materials, hydrolysis is carried out by an enzymatic reaction (Patent Document 2), or a hydrolysis method by using subcritical or supercritical water, etc.

However, when these methods are employed, cellulose or hemicellulose in inedible raw materials is hydrolyzed to obtain a saccharide such as glucose and xylose, as well as a decomposition reaction of these saccharides also proceeds. By the decomposition reaction of the saccharide, a carbonyl compound is produced as a byproduct, and specifically, for example, an aldehyde such as furfural, hydroxymethylfurfural, glycolaldehyde, formic acid, etc., or a ketone such as dihydroxyacetone or benzoquinone, etc., are formed.

Among these, as a method for removing and converting furfural, etc., it has been known a removing method using wood-based carbide or an activated charcoal (Patent Document 3, Non-Patent Document 1), a removing method using a synthetic resin (Patent Document 4), and an a reducing agent an aldehyde-conversion method (Non-Patent Document 2), etc.

PRIOR ART DOCUMENTS

Patent Documents

Patent Document 1: JP Hei. 11-506934A
Patent Document 2: JP 2001-95594A
Patent Document 3: JP 2005-270056A
Patent Document 4: JP 2011-78327A

Non-Patent Documents

Non-Patent Document 1: Maddox I S and Murray A E, Biotechnology Letters vol. 5, No. 3, P 175, 1983
Non-Patent Document 2: Cavka A et al., Biotechnology and Bioengineering, vol. 108, No. 11, P 2592, 2011

SUMMARY OF THE INVENTION

Problems to be Solved by the Invention

Among the carbonyl compounds, furfural or hydroxymethylfurfural, etc., has a property of inhibiting the reaction in the fermentation production process utilizing a microorganism, specifically these compounds cause growth inhibition or fermentation-production inhibition of the microorganism, whereby yield of the fermentation production is lowered. Therefore, these compounds are called as a fermentation inhibitor, and become a big problem when a saccharide solution of inedible raw materials is utilized as a fermentation raw material.

Also, when an organic compound is produced through chemical conversion processes, if a carbonyl compound or an unsaturated alcohol is contained in the saccharide solution, there is a problem that the product is colored.

However, in the removing method using the wood-based carbide or the activated charcoal disclosed in the above-mentioned Patent Document 3 or Non-Patent Document 1, it is difficult to selectively remove the fermentation inhibitor alone, and there are problems that a saccharide concentration is lowered by adsorption of the saccharide, or a cost for production or regeneration of the wood-based carbide or the activated charcoal is required. In addition, in the removing method using the synthetic resin disclosed in the above-mentioned Patent Document 4, since it uses a chromatograph system for removal, there occurs a problem that the process design is restricted.

Further, the reduction removal method using a reducing agent disclosed in the above-mentioned Non-Patent Document 2, in addition to lowness in the reactivity of the reducing agent, the saccharide is also reduced simultaneously with the fermentation inhibitor, and there is a problem that removal of a metal salt by-produced with an equimolar amount to that of the reduced product is necessary, etc.

The present invention has been accomplished in view of the above-mentioned problems, and an object thereof is to provide a method for treating a saccharide solution which can make the saccharide solution applied to a fermentation production process and a chemical conversion process of chemicals excellent production efficiency and process design easy when various kinds of organic compounds are produced by using a solution containing a saccharide (saccharide solution) as a raw material, and a method for producing an organic compound using the saccharide solution obtained by the method.

Means for Solving the Problems

The present inventors have earnestly studied to solve the above-mentioned problems, and as a result, they have found that the above-mentioned problems can be solved by supplying a saccharide solution to a hydrogenation reaction, and subjecting to a processing of hydrogenating at least one selected from a carbonyl compound and an unsaturated alcohol other than a saccharide(s) contained in the saccharide solution, whereby the present invention has been accomplished.

That is, the gist of the present invention resides in,

[1] a method for treating a saccharide solution which comprises subjecting a saccharide solution containing a saccharide and at least one selected from the group consisting of a carbonyl compound and an unsaturated alcohol to hydrogenation reaction to hydrogenate the carbonyl compound and/or the unsaturated alcohol contained in the saccharide solution, wherein the carbonyl compound is other than a saccharide,

[2] the method defined in the above-mentioned [1], wherein the saccharide is comprised of one or more saccharides which is composed of a monosaccharide having 3 to 7 carbon atoms,

[3] the method defined in the above-mentioned [1] or [2], wherein the saccharide solution is derived from inedible raw materials,

[4] the method defined in any one of the above-mentioned [1] to [3], wherein the hydrogenation reaction is carried out in the presence of a metal catalyst,

[5] the method defined in any one of the above-mentioned [1] to [4], wherein the carbonyl compound other than the saccharide is at least one selected from an aldehyde compound and a ketone compound,

[6] the method defined in any one of the above-mentioned [1] to [5], wherein the unsaturated alcohol is an aliphatic conjugated alcohol,

[7] a hydrogenated saccharide solution obtained by the method defined in any one of the above-mentioned [1] to [6],

[8] the hydrogenated saccharide solution defined in the above-mentioned [7], wherein furfural content in the hydrogenated saccharide solution is 0.01% by mass or less based on the total amount of the hydrogenated saccharide solution,

[9] the hydrogenated saccharide solution defined in the above-mentioned [7] or [8], wherein a content of the glycolaldehyde in the above-mentioned hydrogenated saccharide solution is 0.03% by mass or less of the total amount of the hydrogenated saccharide solution,

[10] a method for producing an organic compound, comprising of:

hydrogenating a saccharide solution which is comprised of saccharide and at least one selected from the group consisting of a carbonyl compound and an unsaturated alcohol, wherein the carbonyl compound is other than a saccharide, and producing an organic material in which a microorganism capable of producing an organic material is acted in an aqueous medium on an organic raw material containing the saccharide solution after the step of hydrogenating,

[11] a method for producing an organic compound comprising:

producing an organic material in which a microorganism capable of producing an organic material is acted in an aqueous medium on an organic raw material containing the hydrogenated saccharide solution defined in any one of the above-mentioned [7] to [9],

[12] the method for producing an organic compound defined in the above-mentioned [10] or [11], wherein the step of producing an organic material is carried out under an anaerobic atmosphere,

[13] the method for producing an organic compound defined in any one of the above-mentioned [10] to [12], further comprising of:

purifying the organic compound obtained in the step of producing the organic material,

[14] the method for producing an organic compound defined in any one of the above-mentioned [10] to [13], wherein the above-mentioned aqueous medium is comprised of at least one selected from a carbonate ion, a bicarbonate ion, and a carbon dioxide gas,

[15] the method for producing an organic compound defined in any one of the above-mentioned [10] to [14], wherein the above-mentioned organic compound is at least one selected from an alcohol, an amine, a carboxylic acid and a phenol,

[16] the method for producing an organic compound defined in the above-mentioned [15], wherein the above-mentioned alcohol is an aliphatic alcohol having 2 to 10 carbon atoms,

[17] the method for producing an organic compound defined in the above-mentioned [15], wherein the above-mentioned carboxylic acid is an aliphatic carboxylic acid having 2 to 10 carbon atoms,

[18] a method for culturing a microorganism capable of producing a useful substance, comprising of:

culturing the microorganism with, the hydrogenated saccharide solution defined in any one of the above-mentioned [7] to [9] is used as a carbon source,

[19] the method defined in any one of the above-mentioned [10] to [18], wherein the above-mentioned microorganism is at least one selected from the group consisting of coryneform bacterium, *Escherichia coli*, a bacterium of the genus *Anaerobiospirillum*, a bacterium of the genus *Actinobacillus*, a bacterium of the genus *Mannheimia*, a bacterium of the genus *Basfia*, a bacterium of the genus *Zymomonas*, a bacterium of the genus *Zymobacter*, a fungus and a yeast,

[20] the method defined in any one of the above-mentioned [10] to [19], wherein the above-mentioned microorganism can utilize pentose nutritionally,

[21] the method defined in the above-mentioned [20], wherein the above-mentioned pentose is xylose,

[22] the method defined in the above-mentioned [21], wherein the above-mentioned microorganism is a microorganism in which a xylose isomerase activity is provided or enhanced,

[23] the method defined in the above-mentioned [22], wherein the above-mentioned microorganism is a microorganism in which a xylulokinase activity is provided or enhanced.

Effect of the Invention

According to the method for treating a saccharide solution of the present invention, contents of the carbonyl compound and the unsaturated alcohol in the saccharide solution can be reduced, so that if the obtained saccharide solution is used in a fermentation production process utilizing a microorganism, yield of the objective organic compound can be improved.

Also, when an organic raw material containing the hydrogenated saccharide solution of the present invention is used, production efficiency in producing the organic compound by the fermentation production process can be improved.

Further, coloring of the organic compound which is a product utilized in the chemical conversion process can be suppressed.

Moreover, when the method for producing the organic compound of the present invention is employed, a desired organic compound can be produced with a relatively simple processing with high production efficiency.

Furthermore, when the culturing method of the present invention is employed, an amount of the fermentation inhibitor in the fermentation production process can be reduced, so that the proliferation yield and the proliferation rate of the microorganism can be improved, whereby fermentation productivity can be improved.

BRIEF DESCRIPTION OF THE DRAWING

FIG. 1 shows absorption spectra of the saccharide solution of Preparation example 9 and hydrogenated saccharide solutions of Examples 41 and 42.

BEST MODE TO CARRY OUT THE INVENTION

In the following, the present invention is explained in more detail, but the present invention is not limited by the following embodiments, and can be practiced by changing variously so long as it is within the range of the gist of the present invention.

<First Invention: A Method for Treating a Saccharide Solution>

The first invention of the present invention comprises applying a solution containing a saccharide(s) (in the following, it is referred to as "saccharide solution".) to hydrogenation reaction, whereby at least one selected from the group consisting of a carbonyl compound and an unsaturated alcohol other than the saccharide(s) contained in the saccharide solution is hydrogenated.

The saccharide solution in the first invention, and a "saccharide solution" used in the second invention, the third invention and the fourth invention (the first to the fourth inventions are sometimes collectively called "the present invention".) mentioned below mean a liquid containing a saccharide(s) as mentioned above, preferably an aqueous solution containing a saccharide(s). In the following, the saccharide contained in the saccharide solution is firstly explained.

(Saccharide)

The saccharide contained in the saccharide solution to be used in the present invention is not particularly limited, and the so-called general saccharides may be employed, preferably a saccharide in which a microorganism can utilize it as a carbon source. More specifically, there may be mentioned monosaccharides (triose) having 3 carbon atoms such as glyceraldehyde, etc.; monosaccharides (tetrose) having 4 carbon atoms such as erythrose, threose, erythrulose, etc.; monosaccharide (pentose) having 5 carbon atoms such as ribose, lyxose, xylose, arabinose, deoxyribose, xylulose, ribulose, etc.; monosaccharides (hexose) having 6 carbon atoms such as allose, talose, gulose, glucose, altrose, mannose, galactose, idose, fucose, fuculose, rhamnose, psicose, fructose, sorbose, tagatose, etc.; monosaccharide (heptose) having 7 carbon atoms such as assedoheptulose, etc.; disaccharides such as sucrose, lactose, maltose, trehalose, turanose, cellobiose, etc.; trisaccharides such as raffinose, melezitose, maltotriose, etc.; oligosaccharides such as fructooligosaccharide, galactooligosaccharide, mannan oligosaccharide, etc.; polysaccharides such as starch, dextrin, cellulose, hemicellulose, glucan, pentosan, etc.; and the like.

The saccharide solution to be used in the present invention may contain one kind of the above-mentioned saccharide or two or more kinds thereof.

The saccharide to be used in the present invention preferably contain one or more saccharides which is composed of a monosaccharide having 3 to 7 carbon atoms. This is because these saccharides are easily utilized as a carbon source of a microorganism. It is more preferred that the saccharide contains such a saccharide as a main component. The main component means a component which occupies generally 50% by mass or more based on the total mass of the saccharide, more preferably a component which occupies 70% by mass or more and 100% by mass or less.

Incidentally, "the saccharide which is composed of a monosaccharide having 3 to 7 carbon atoms as a constitutional component" means a monosaccharide having 3 to 7 carbon atoms, a polysaccharide which is composed of monosaccharides having 3 to 7 carbon atoms, or a mixture thereof. Among these, a hexose, a pentose and a disaccharide composed of a hexose or a pentose are more preferred. Since these are main constitutional components of the plants in the natural world, these exist abundantly and raw materials can be easily obtained.

As the above-mentioned hexose, glucose, fructose, mannose or galactose is preferred, and glucose is more preferred. As the pentose, xylose or arabinose is preferred, and xylose is more preferred. As the disaccharide, sucrose is preferred. Since glucose, xylose and sucrose are main constitutional components of the natural world or the plants, raw materials can be easily obtained.

(Source and Preparation Method of Saccharide Solution)

A method for producing the saccharide solution to be used in the present invention is not particularly limited, and may be mentioned, for example, a method for producing the same by dissolving one or more kinds of the above-mentioned saccharide(s) in water, or a method for producing the same by decomposing a raw material containing the above-mentioned saccharide(s) as constitutional components (hereinafter also referred to as "saccharide raw material".) to a saccharide which is a constitutional unit thereof. The saccharide raw material is not particularly limited, and more specifically mentioned polysaccharides such as cellulose, hemicellulose, starch, etc., or plants comprising the polysaccharides as constitutional units, etc. In addition, a starch scarified solution or molasses, etc., is also used, and more specifically mentioned a saccharide solution squeezed from the plant such as saccharide cane, saccharide beets or saccharide maple, etc.

The above-mentioned saccharide raw material can be classified into "edible raw materials" and "inedible raw materials" in the viewpoint that it can edible or not.

As the edible raw materials, there may be mentioned saccharide cane, starch, saccharide beets, corn, potato, cassava, saccharide maple, etc.

As the inedible raw materials, there may be more specifically mentioned, bagasse, switchgrass, napier grass, erianthus, corn stover, rice straw, wheat straw, rice bran, timber, wood, vegetable oil residue, switch cane, bamboo, pulp, waste paper, food waste, fishery product residue, livestock waste, etc.

Among these, the inedible raw materials are preferred in the points that they do not compete with an edible use different from the edible raw materials, and stable supply and effective utilization of resources can be performed since they are generally disposed or subjected to incineration processing in many cases.

A method for obtaining a saccharide from the above-mentioned saccharide raw material is not particularly limited and may be mentioned, for example, a method of hydrolyzing a starch aqueous solution by adding dil. sulfuric acid, a method of producing by enzymolysis of a starch aqueous solution using various enzymes, a method of hydrolyzing cellulose or hemicellulose to a monosaccharide such as a hexose represented by glucose or a pentose represented by xylose using conc. sulfuric acid, a method in which after subjecting to a pretreatment to improve reactivity of a saccharide raw material, it is hydrolyzed by an enzymatic reaction, subcritical water, supercritical water, etc. It is also possible to use waste molasses which remains after recovering sugar from molasses generating in the manufacturing process of sugar as a saccharide solution.

A concentration of the saccharide contained in the saccharide solution of the present invention markedly varies depending on the origin of the saccharide solution or a kind of the saccharide to be contained, etc., and is not particularly limited, but in consideration with the productivity in the fermentation production process and the chemical conversion process, the total concentration of the saccharide is generally 0.1% by mass or more, preferably 2% by mass or more, and generally 60 mass % or less, and preferably 50 mass % or less.

The saccharide solution to be used in the present invention is a solution containing the above-mentioned saccharide, and may contain other component(s) than water and the saccharide(s). Other component(s) is/are not specifically limited and, for example, byproducts other than the saccharide or impurities, which are generated at the time of obtaining the saccharide from the saccharide raw material, may be contained. More specifically, there may be mentioned a carbonyl compound other than the saccharide mentioned later, an alcohol compound such as an unsaturated alcohol, etc.; a phenol compound derived from lignin; an alkali metal compound, an alkaline earth metal compound, a nitrogen compound, a sulfur compound, a halogen compound, an inorganic compound such as a sulfate ion, etc.

Incidentally, the saccharide solution to be used in the present invention is not particularly limited as long as it is a liquid containing the above-mentioned saccharide, but with regard to a solid component such as lignin-derived, etc., it is preferably removed by using filtration or adsorption, etc. In addition, the saccharide solution to be used in the present invention may be used by lowering a saccharide concentration by diluting with water depending on the purposes to be used, or used by heightening the saccharide concentration by additionally adding the saccharide or condensation of the solution.

(Carbonyl Compound Other than Saccharide)

In the saccharide solution to be used in the present invention, a carbonyl compound other than the saccharide is generally contained, which is formed at the time of producing the saccharide solution and storing the same. As the carbonyl compound, it is not particularly limited as long as it has a carbonyl group in the structure, and may be an aliphatic carbonyl compound or a compound having an aromatic group. It is preferably a carbonyl compound having 1 to 20 carbon atoms, more preferably 16 or less carbon atoms, further preferably 12 or less carbon atoms. The carbonyl compound in the above-mentioned range has a relatively high water-solubility, and contained in the saccharide solution, in particular, it is contained in an aqueous solution containing a saccharide in many cases. Specific examples of such a carbonyl compound may be mentioned, for example, an aldehyde compound such as furfural, hydroxymethylfurfural, glycolaldehyde, formic acid, hydroxybenzaldehyde, syringaldehyde, vanillin, isovanillin, orthovanillin, coniferyl aldehyde, etc.; a ketone compound such as 1,4-benzoquinone, etc.; an unsaturated ester compound, preferably an unsaturated conjugated ester compound such as methyl acrylate, ethyl acrylate, etc.; an aldehyde compound and a ketone compound are preferred, and more preferably an aldehyde compound.

(Unsaturated Alcohol)

In the saccharide solution to be used in the present invention, an unsaturated alcohol is generally contained in the saccharide solution, which is formed at the time of producing the saccharide solution and storing the same. The unsaturated alcohol is not particularly limited as long as it has an aliphatic carbon-carbon double bond (olefin) in the structure, and it may be an aliphatic unsaturated alcohol or a compound having an aromatic group. It is preferably an unsaturated alcohol having 1 to 20 carbon atoms, more preferably 16 or less carbon atoms, further preferably 12 or less carbon atoms. The alcohol in the above-mentioned range has a relatively high water-solubility, and contained in the saccharide solution, in particular, it is contained in an aqueous solution containing a saccharide in many cases. In addition, the unsaturated alcohol may have a conjugated structure in the structure. It may be typically mentioned an aliphatic conjugated alcohol. Specific examples of the unsaturated alcohol may be mentioned 2-alkenyl alcohol, more specifically allyl alcohol, crotyl alcohol, 2-penten-1-ol, 2-hexen-1-ol, 2-hepten-1-ol, etc., preferably allyl alcohol or crotyl alcohol.

The present inventors have found that at least one selected from the above-mentioned carbonyl compound and the unsaturated alcohol causes lowering or decreasing in a produced amount, an accumulated amount and a production rate of a useful compound, in the process of producing an organic compound by fermentation using a saccharide solution as a raw material (a process for producing an organic material). In the following, a substance that has an action as mentioned above in the above-mentioned process for producing an organic material is collectively called "the fermentation inhibitor". In the saccharide solution containing the above-mentioned fermentation inhibitor, lowering in the proliferation yield or the proliferation rate occurs in the culturing process of the microorganism.

The inventors have found that the carbonyl compound or the unsaturated alcohol causes coloring of the product due to their high reactivity in the process of producing an organic compound through the chemical conversion process. With regard to the coloring, the carbonyl compound, typically an aldehyde compound such as furfural, etc., causes remarkable coloring, so that if these carbonyl compounds, preferably an aldehyde compound, more preferably furfural is/are removed, coloring of the product can be suppressed.

(Hydrogenation Reaction)

In the first invention, at least one selected from the above-mentioned carbonyl compound and the unsaturated alcohol contained in the above-mentioned saccharide solution is supplied to the hydrogenation reaction to reduce these compounds. According to this procedure, the above-mentioned carbonyl compound and the unsaturated alcohol are converted into hydrogenated substances, respectively, whereby the contents thereof can be reduced. Incidentally, "the hydrogenation reaction" in the first invention means a chemical reaction in which at least one selected from the group consisting of the carbonyl compound and the unsaturated alcohol other than the saccharide contained in the above-mentioned saccharide solution is/are supplied to a hydrogen atmosphere to convert the same into a hydrogenated substance(s).

In the above-mentioned hydrogenation reaction, at least one selected from the group consisting of the carbonyl compound and the unsaturated alcohol other than the saccharide contained in the saccharide solution is/are reduced by hydrogen to be converted into the corresponding hydride(s). This is because these compounds show high fermentation inhibition to the microorganism in many cases in the third invention and the fourth invention mentioned later.

The terms "corresponding hydride(s)" herein mentioned are collective terms of the substances in which the above-mentioned carbonyl compound and/or the unsaturated alcohol is/are converted by hydrogenation, preferably those in which fermentation inhibition thereof is reduced as compared with that before the hydrogenation.

In the treatment method of the present invention, it may be sufficient if at least one selected from the group consisting of the above-mentioned carbonyl compound and the unsaturated alcohol is hydrogenated and converted into the corresponding hydride(s), and it is preferred that fermentation inhibition when the saccharide solution is used for the above-mentioned fermentation production is reduced. A degree of fermentation inhibition of the saccharide solution can be preferably measured by using the contents of the above-mentioned carbonyl compound and the unsaturated alcohol, or the hydride(s) thereof contained in the saccharide solution as an index, which is mentioned later.

Specific examples of "the hydride(s)" are as follows. The above-mentioned aldehyde compound is converted into the corresponding primary alcohol by the hydrogenation reaction, and the ketone compound is converted into the corresponding secondary alcohol by the same. These hydrides (alcohols) may be further converted into a dehydrated compound from the respective alcohols by further hydrogenation. Also, an unsaturated ester compound is generally converted into an ester compound in which the carbon-carbon double bond has been hydrogenated by the hydrogenation reaction. Further, it may be converted into the corresponding alcohol by the further hydrogenation. A hydride corresponding to the unsaturated ester compound may be either of the above.

Moreover, according to the hydrogenation reaction, the unsaturated alcohol is converted into an alcohol in which the carbon-carbon double bond has been hydrogenated, preferably converted into a saturated alcohol.

By supplying the saccharide solution to the above-mentioned hydrogenation reaction, an inhibition effect in the fermentation production of the organic compound can be reduced, and a fermentation process of the saccharide solution can be carried out without reducing the proliferation rate or the proliferation yield in the culturing process of the microorganism. In addition, in the chemical conversion process, the carbonyl compound or the unsaturated alcohol having high reactivity is converted, coloring, etc., of the product can be suppressed.

(Metal Catalyst)

The hydrogenation reaction in the first invention is preferably carried out in the presence of a catalyst. A kind of the catalyst is not particularly limited, and it may be a material having an ability of hydrogenating the carbonyl group of the carbonyl compound other than the above-mentioned saccharide, or the carbon-carbon double bond possessed by the unsaturated alcohol and the unsaturated ester compound, etc., and there may be mentioned, for example, a metal catalyst, an organic molecule catalyst, etc.

The above-mentioned hydrogenation treatment is preferably carried out in the presence of a metal catalyst. The metal catalyst means a material in which the metal becomes a catalyst activity species. A metal carrying catalyst which is a catalyst in which the above-mentioned metal is carried on a carrier is more preferred.

A form of the metal of the above-mentioned metal catalyst is not particularly limited as long as it is a metal state when the hydrogenation reaction in the present invention is carried out.

With regard to the kind of the metal of the above-mentioned metal catalyst, it is not particularly limited as long as it can hydrogenate the carbonyl group of the carbonyl compound other than the above-mentioned saccharide and the carbon-carbon double bond possessed by the unsaturated alcohol and the unsaturated ester compound, etc., and it is desirably contains a metal element(s), for example, of Group 8 to Group 11 of the Periodic Table.

More specifically, it is ruthenium, palladium, rhodium, platinum, nickel, copper, iridium, gold, etc., preferably ruthenium, palladium, rhodium, platinum, nickel, copper, more preferably ruthenium, palladium.

The catalyst using ruthenium has high hydrogenation ability to the carbonyl compound such as the aldehyde compound, the ketone compound, etc., and the catalyst using palladium is, in addition to high hydrogenation ability of the carbonyl compound, preferred in the point that it is a metal having high hydrogenation ability which can hydrocrack the alcohol obtained by the reduction of the carbonyl compound or the unsaturated alcohol.

The above-mentioned metal may be used one kind or two or more kinds of metals as long as it does not inhibit the effects of the present invention, and a ratio to be used is also not limited.

The above-mentioned metal catalyst is preferably used as a metal carrying catalyst since recovery of the catalyst is easy, stability is high and in the point of a catalyst lifetime. A carrier to be used for the above-mentioned metal carrying catalyst is not particularly limited, and may be used, for example, a carbonaceous carrier such as activated charcoal, carbon black, and SiC, etc.; metal oxides such as alumina, silica, diatomaceous earth, zirconia, titania, etc.; and among these, the carbonaceous carrier or alumina, silica is preferred in the point of stability of the metal carrying catalyst.

A content of metal in the metal carrying catalyst is not particularly limited, and in general, in terms of mass percentage calculated on a metal, based on the total mass of the carrier and the metal (based on the whole mass of the catalyst), and in terms of mass percentage of each metal atom based on the carrier, it is generally 0.1% by mass or more, preferably 0.5% by mass or more, more preferably 1% by mass or more, and is generally 50% by mass or less, preferably 20% by mass or less, more preferably 10% by mass or less. Incidentally, when two or more kinds of the metals are contained, the content of the two or more kinds of the metals is preferably within the above-mentioned range.

A method for producing the metal carrying catalyst is not particularly limited as long as the metal is carried on a carrier, and in general, a catalyst is produced by introducing a metal salt into a carrier according to the operation that the carrier is dipped into a solution of the metal salt, and converting it to a metal according to the reduction treatment with a liquid phase or a vapor phase.

A shape of the catalyst to be used in the present invention is not particularly limited, and may be optionally selected according to a fixed bed system, a fluidized bed system, a liquid phase reaction, a vapor phase reaction, more specifically, it may be used in the state of powder, crashed state, pellets, etc.

(Hydrogenation Reaction Condition)

The conditions of the hydrogenation reaction in the first invention is not particularly limited as long as the carbonyl group or the carbon-carbon double bond of the carbonyl compound and the unsaturated alcohol other than the saccharide, which are fermentation inhibitors in the saccharide solution is hydrogenated.

The saccharide contained in the saccharide solution also has an aldehyde group, etc., and when these are similarly hydrogenated, a saccharide alcohol is formed. More specifically, sorbitol is formed from glucose, and xylitol is formed from xylose. That is, even if the above-mentioned saccharide alcohol is formed, if it does not cause any problem in the process of fermentation producing a useful compound or in the culturing process of the microorganism mentioned later, the conditions of the hydrogenation reaction are not limited. Therefore, it is preferred to select selective hydrogenation conditions which can hydrogenate the carbonyl group of the carbonyl compound other than the saccharide and the carbon-carbon double bond possessed by the unsaturated alcohol or the unsaturated ester compound, but can difficultly hydrogenate the saccharide such as glucose and xylose, etc.

A reaction temperature of the hydrogenation reaction in the first invention is not particularly limited, and is generally 20° C. or higher, preferably 40° C. or higher, more preferably 50° C. or higher and is generally 120° C. or lower, preferably 100° C. or lower, more preferably 90° C. or lower. By carrying out the hydrogenation reaction within the above-mentioned temperature range, without hydrogenating the saccharide, it is possible to hydrogenate the carbonyl component other than the saccharide and the carbonyl group and the carbon-carbon double bond such as the aliphatic conjugated alcohol, etc., which are fermentation inhibiting components.

The hydrogenation reaction in the first invention is generally carried out in the presence of a hydrogen gas under the condition of pressurization. A pressure of the hydrogenation reaction is not particularly limited, and is generally 0.1 MPa or more, preferably 0.3 MPa or more, more preferably 0.4 MPa or more and is generally 10 MPa or less, preferably 5 MPa or less, more preferably 3 MPa or less. In general, if a reaction pressure is increased, a reaction rate of the hydrogenation is increased, and hydrogenation of a fermentation inhibitor is promoted, but formation of a saccharide alcohol is also promoted, so that it is desired that the hydrogenation is desirably carried out under lower pressure conditions when the formation of the saccharide alcohol is to be suppressed.

An amount of the catalyst to be used in the hydrogenation reaction of the first invention is not particularly limited, and is determined by various conditions such as a concentration of a fermentation inhibiting component in the saccharide solution, a concentration of a catalyst poisoning component in the saccharide solution, a kind of the metal of the catalyst to be used, a carried amount of the metal of the catalyst, a reaction temperature, a reaction pressure, a reaction format and a treated amount of the saccharide solution, and desired reaction performance such as a removal efficiency of the fermentation inhibiting component, suppression of formation of the saccharide alcohol, etc.

A reaction time of the hydrogenation reaction in the first invention is not particularly limited, and is determined by various conditions such as a concentration of the fermentation inhibiting component in the saccharide solution, a concentration of the catalyst poisoning component in the saccharide solution, a kind of a metal of the catalyst to be used, a carried amount of the metal of the catalyst, a reaction temperature, a reaction pressure, a reaction format and a treated amount of the saccharide solution, and desired reaction performance such as a removal efficiency of the fermentation inhibiting component, suppression of formation of the saccharide alcohol, etc. However, if the reaction time is short, there is a possibility of not proceeding conversion of the fermentation inhibitor sufficiently, while if the reaction time is long, there is a possibility of increasing a formation amount of the saccharide alcohol.

In the hydrogenation reaction of the first invention, a solvent may be used and a kind thereof is not particularly limited, and water is generally used. An organic solvent may be used as a cosolvent, but there is a possibility of causing fermentation inhibition by migrating the organic solvent into the aqueous phase. Thus, a process for removing the organic solvent is necessary when the material is supplied to the fermentation production or the culturing process of the microorganism so that the saccharide solution is desirably subjected to the hydrogenation treatment as the aqueous solution as such.

In the hydrogenation reaction of the first invention, if a catalyst poisoning component such as an N component, an S component, an acid, etc., is contained in the saccharide solution, and if a catalyst is used at the time of the hydrogenation reaction, there is a possibility that the hydrogenation activity is lowered by adsorbing to the catalyst. Such a catalyst poisoning component may be removed before subjecting to the hydrogenation treatment. The method of removal is not particularly limited, and an adsorption removal treatment by using an ion exchange resin, activated charcoal or a synthetic resin, etc., may be carried out.

<Second Invention: Hydrogenated Saccharide Solution>

In the hydrogenation reaction of the above-mentioned first invention, at least one selected from the group consisting of the carbonyl compound and the unsaturated alcohol other than the saccharide contained in the saccharide solution is reduced by the hydrogenation reaction, so that a concentration(s) of the above-mentioned carbonyl compound and/or the unsaturated alcohol in the obtained saccharide solution is/are lower than the concentration thereof in the initial saccharide solution. Incidentally, the saccharide solution after supplying to the above-mentioned hydrogenation reaction is sometimes called as "the hydrogenated saccharide solution" in some cases.

Among the carbonyl compound and/or the unsaturated alcohol other than the saccharide contained in the hydrogenated saccharide solution of the second invention, there may be mentioned furfural as a substance having high fermentation inhibiting ability to the microorganism. A content of the furfural in the saccharide solution (hydrogenated saccharide solution) after the hydrogenation reaction is preferably as little as possible, and preferably 0.01% by mass or less based on the whole amount of the hydrogenated saccharide solution, more preferably 0.001% by mass or less. In addition, by making the content of the furfural little, coloring of the saccharide solution can be suppressed, and when the organic compound is to be produced through the chemical conversion process, coloring of the forming organic compound can be suppressed.

Also, among the carbonyl compound and/or the unsaturated alcohol other than the saccharide contained in the hydrogenated saccharide solution of the second invention, there may be mentioned glycolaldehyde as the other substance having high fermentation inhibiting ability to the microorganism. The glycolaldehyde may be a monomer or a dimer, and in the case of an aqueous solution, it may be a hydrated compound. In general, it becomes an equilibrium mixture of these compounds. A content of the glycolaldehyde in the hydrogenated saccharide solution is preferably 0.03% by mass or less based on the whole amount of the hydrogenated saccharide solution, more preferably 0.01% by mass or less.

By removing the carbonyl compound and the unsaturated alcohol other than the above-mentioned saccharide within the above-mentioned range, growth of the microorganism or an efficiency of the fermentation production of the useful compound can be improved in the fermentation process mentioned later.

The hydrogenated saccharide solution of the second invention may contain a hydride(s) of the carbonyl compound and/or the unsaturated alcohol other than the above-mentioned saccharide in the saccharide solution, and more specifically, when they are the aldehyde compound and the ketone compound, it may contain a corresponding alcohol, a compound further dehydrated from the alcohol by hydrocracking, etc. More specifically, as the hydrogenated product of the furfural, furfuryl alcohol or tetrahydrothrfilryl alcohol may be mentioned, and as a compound in which these alcohols are dehydrated, methylfuran or dimethylfuran may be mentioned. As the hydrogenated product of the glycolaldehyde, ethylene glycol may be mentioned. Similarly, when it is a ketone, a corresponding alcohol is contained, and when it is an unsaturated ester compound, an ester compound in which a carbon-carbon double bond in the ester has been hydrogenated, or an alcohol in which these esters are further reduced may be contained. Also, when it is the unsaturated alcohol, an alcohol in which the unsaturated carbon double bond has been hydrogenated, and a compound in which the alcohol is further hydrogenated by hydrocracking, etc., may be contained.

The hydrogenated saccharide solution of the second invention can be obtained by supplying the saccharide solution to the hydrogenation reaction, when a catalyst is used at the time of the hydrogenation reaction, a process of separating and recovering the used catalyst is contained. As the separating method of the catalyst, in the case of a batchwise reaction, in general, the obtained hydrogenated saccharide solution is filtrated to recover the catalyst. Also, in the case of a flow-through reaction, the saccharide solution is developed to a fixed bed reactor, etc., whereby the catalyst and the hydrogenated saccharide solution can be separated and recovered. Further, the hydrogenated saccharide solution of the second invention may be optionally treated by the means such as an ion exchange resin, activated charcoal, a synthetic resin, etc., if necessary.

The catalyst recovered after the hydrogenation reaction can be used for repeated use in a batchwise reactor or continuous use in a continuous reactor as long as it can maintain the activity of hydrogenating or hydrocracking of the carbonyl compound or the carbon-carbon double bond of the unsaturated alcohol or the unsaturated ester other than the saccharide.

On the other hand, the catalyst lowered in activity can maintain the activity by the operation conditions of raising the hydrogen pressure or raising the reaction temperature, etc. However, it is necessary to control the activity which hydrogenates the fermentation inhibiting component while suppressing formation of the saccharide alcohol.

The hydrogenated saccharide solution of the second invention according to the present invention can be used at the time of producing the organic compound of the third invention mentioned later. It can be similarly used in the chemical conversion process to produce various kinds of the organic compounds.

The chemical conversion process herein mentioned means a chemical reaction in general which can convert the saccharide contained in the hydrogenated saccharide solution as a raw material into various kinds of the organic compounds. A kind of the chemical reaction is not particularly limited, and more specifically, there may be mentioned an oxidation reaction of obtaining aldonic acid in which a carbonyl group possessed by the saccharide is oxidized, or obtaining aldaric acid in which a hydroxymethyl group is further converted into a carboxyl group, etc., a reduction reaction of obtaining a saccharide alcohol in which a carbonyl group possessed by the saccharide is reduced, a reaction of converting into various kinds of the organic compounds by acting an acid, an alkali, various kinds of catalysts thereon, and the like.

<Third Invention: Method for Producing Organic Compound>

The third invention of the present invention is a method for producing an organic compound by acting a microorganism having an ability of producing a useful substance on an organic raw material containing a saccharide solution.

(Hydrogenating Treatment Process)

In the third invention, when the saccharide solution containing at least one selected from the group consisting of the carbonyl compound and the unsaturated alcohol other than the saccharide is used, the third invention comprises a process (a hydrogenating treatment process) in which the saccharide solution is firstly supplied to the hydrogenation reaction, to hydrogenate at least one selected from the group consisting of the carbonyl compound and the unsaturated alcohol other than the saccharide contained in the saccharide solution.

The saccharide in the above-mentioned hydrogenating treatment process, the carbonyl compound and the unsaturated alcohol other than the saccharide, and the metal catalyst to be used in the hydrogenating treatment process and the conditions of the hydrogenation treatment, etc., may be used those explained in the above-mentioned first invention (treatment method of saccharide) and the conditions as such.

On the other hand, in the third invention, it is possible to use the hydrogenated saccharide solution of the second invention as the saccharide solution. In this case, the above-mentioned hydrogenating treatment process can be omitted.

(Process for Producing Organic Material)

The third invention contains a process for producing an organic material which comprises acting a microorganism having an organic material producing ability on the saccharide solution after the above-mentioned hydrogenation treatment or an organic raw material containing the hydrogenated saccharide solution of the second invention to obtain the organic compound. The organic raw material to be used in the process for producing an organic material contains a saccharide solution which has been subjected to the hydrogenation treatment, and at the time of forming the organic compound, various kinds of components may be optionally added to the saccharide solution which has been subjected to the hydrogenation treatment depending on the characteristics of the saccharide solution, or a kind of the organic compound to be produced or the microorganism to be acted depending on necessity. As the materials to be further added to the saccharide solution which has been subjected to the hydrogenation treatment in the third invention, there may be mentioned a carbon source capable of forming the organic compound to which a microorganism having an ability of producing a useful substance mentioned later can assimilate, and a kind thereof is not particularly limited, and is generally mentioned fermentable carbohydrates including a carbohydrate such as galactose, lactose, glucose, fructose, sucrose, starch and cellulose, etc.; and a polyalcohol such as glycerol, mannitol, xylitol and ribitol, etc. Among these, glucose, sucrose or fructose is preferred, and glucose or sucrose is particularly preferred.

These may be added singly, or may be added in combination.

A using concentration of the organic raw material in the process for producing an organic material is not particularly limited, and preferably as high as possible in the range which does not inhibit formation of the organic compound. More specifically, a concentration of the organic raw material containing the saccharide solution is generally 50 g/L or more, preferably 100 g/L or more, and is generally 300 g/L or less, preferably 200 g/L or less based on the whole volume of the aqueous medium. Also, based on the whole amount of the culture solution, it may be used within the range of generally 1 to 100 g/L, preferably 5 to 50 g/L. The organic raw material may be further added to the aqueous medium to compensate the decrease of the organic raw material due to the progress of the reaction.

(Microorganism Having Ability of Producing Useful Substance)

The microorganism to be used in the third invention is not particularly limited so long as it is a microorganism having an ability of producing a useful substance.

Incidentally, "the microorganism having an ability of producing a useful substance" in the third invention means a microorganism which can form and accumulate a useful substance in a medium when the microorganism is cultured in the medium.

(Useful Substance)

The useful substance produced by the microorganism is not particularly limited so long as it is an organic compound which can be formed by the microorganism in a medium and accumulated, and specifically mentioned an alcohol such as ethanol, propanol, butanol, 1,2-propanediol, 1,3-propanediol, 1,3-butanediol, 2,3-butanediol, 1,4-butanediol, 1,5-pentanediol, 1,6-hexanediol, glycerol, erythritol, xylitol, sorbitol, etc.; an amine such as 1,5-pentamethylenediamine, 1,6-hexamethylenediamine, etc.; a carboxylic acid such as acetic acid, butyric acid, glycolic acid, lactic acid, 3-hydroxypropionic acid, pyruvic acid, succinic acid, fumaric acid, malic acid, oxaloacetic acid, cis-aconitic acid, citric acid, isocitric acid, 2-oxoglutaric acid, 2-oxoisovaleric acid, glutaric acid, itaconic acid, adipic acid, levulinic acid, quinic acid, shikimic acid, acrylic acid, methacrylic acid, etc.; an amino acid such as alanine, valine, leucine, isoleucine, lysine, arginine, methionine, histidine, cysteine, serine, threonine, glutamic acid, aspartic acid, glutamine, asparagine, phenylalanine, tyrosine, proline, tryptophan, etc.; a phenol such as phenol, catechol, hydroquinone, etc.; an aromatic carboxylic acid such as benzoic acid, 4-hydroxybenzoic acid, protocatechuic acid, phthalic acid, isophthalic acid, terephthalic acid, etc.; a nucleoside such as inosine, guanosine, etc., a nucleotide such as inosinic acid, guanylic acid, etc.; and an unsaturated hydrocarbon compound such as isobutylene, isoprene, butadiene, etc.

Among these, an alcohol, an amine, a carboxylic acid or a phenol is preferred since the conventionally known method as the fermentation production can be employed and it can be used as the resin raw material, and an aliphatic alcohol having 2 to 10 carbon atoms and an aliphatic carboxylic acid having 2 to 10 carbon atoms are more preferred. Above all, ethanol, butanediol or succinic acid is more preferred since fermentation productivity is good.

(Microorganism)

The microorganism to be used in the third invention is not particularly limited so long as it is a microorganism having an ability of producing a useful substance, and preferably at least one microorganism selected from the group consisting of coryneform bacterium, *Escherichia coli*, a bacterium of the genus *Bacillus*, a bacterium of the genus *Klebsiella*, a bacterium of the genus *Serratia*, a bacterium of the genus *Clostridium*, a bacterium of the genus *Enterobacter*, a bacterium of the genus *Ralstonia*, a bacterium of the genus *Anaerobiospirillum*, a bacterium of the genus *Actinobacillus*, a bacterium of the genus *Mannheimia*, a bacterium of the genus *Basfia*, a bacterium of the genus *Zymomonas*, a bacterium of the genus *Zymobacter*, a filamentous fungus and a yeast fungus.

Among these, at least one selected from the group consisting of coryneform bacterium, *Escherichia coli*, a bacterium of the genus *Bacillus*, a bacterium of the genus *Anaerobiospirillum*, a bacterium of the genus *Actinobacillus*, a bacterium of the genus *Mannheimia*, a bacterium of the genus *Basfia*, a bacterium of the genus *Zymobacter*, a filamentous fungus and a yeast fungus is preferred, more preferably coryneform bacterium, *Escherichia coli*, a yeast fungus, further preferably coryneform bacterium.

The above-mentioned coryneform bacterium is not particularly limited as long as it is a bacterium classified thereinto, and may be mentioned a bacterium belonging to *Corynebacterium*, a bacterium belonging to *Brevibacterium*, a bacterium belonging to *Arthrobacter*, etc., and among these, there may be preferably mentioned those belonging to *Corynebacterium* and *Brevibacterium*, further preferably bacteria classified into *Corynebacterium glutamicum*, *Brevibacterium flavum*, *Brevibacterium ammoniagenes* or *Brevibacterium lactofermentum*.

Among the coryneform bacterium usable in the third invention, particularly preferred specific examples may be mentioned *Brevibacterium flavum* MJ-233 (FERM BP-1497), Ditto MJ-233 AB-41 (FERM BP-1498), *Brevibacterium ammoniagenes* ATCC6872, *Corynebacterium glutamicum* ATCC31831, and *Brevibacterium lactofermentum* ATCC13869, etc. Incidentally, *Brevibacterium flavum* is now classified into *Corynebacterium glutamicum* in some cases (Lielbl W, Ehrmann M, Ludwig W, Schleifer K H, Int J Syst Bacteriol., 1991, Vol. 41, p 255-260), so that in the present invention, *Brevibacterium flavum* strain MJ-233, and its mutant strain MJ-233 AB-41 are deemed to be the same strain as *Corynebacterium glutamicum* strain MJ-233 and strain MJ-233 AB-41, respectively.

The above-mentioned *Brevibacterium flavum* MJ-233 was deposited on Apr. 28, 1975 at National Institute of Bioscience and Human-Technology, the Agency of Industrial Science and Technology, Ministry of International Trade and Industry (now National Institute of Technology and Evaluation, Patent Microorganisms Depositary Center) (〒305-8566 Chuo 6, 1-1, Higashi 1-chome, Tsukuba-shi, Ibaraki-ken, Japan) as a deposition number of FERM P-3068, and transferred to the International Deposition based on the Budapest Treaty on May 1, 1981, and deposited under the accession number FERM BP-1497.

As the *Escherichia coli* usable in the third invention, there may be mentioned *Escherichia coli*, etc. Also, as the bacterium of the genus *Anaerobiospirillum* usable in the third invention, there may be mentioned *Anaerobiospirillum succiniciproducens*, etc.

Further, as the bacterium of the genus *Bacillus* usable in the third invention, there may be mentioned *Bacillus subtilis, Bacillus licheniformis, Bacillus amyloliquefaciens*, etc.

Moreover, as the bacterium of the genus *Klebsiella* usable in the third invention, there may be mentioned *Klebsiella pneumoniae, Klebsiella oxytoca*, etc.

Furthermore, as the bacterium of the genus *Serratia* usable in the third invention, there may be mentioned *Serratia marcescens*, etc.

Also, as the bacterium of the genus *Clostridium* usable in the third invention, there may be mentioned *Clostridium acetobutylicum, Clostridium autoethanogenum, Clostridium ljungdahlii, Clostridium ragsdalei*, etc.

Further, as the bacterium of the genus *Enterobacter* usable in the third invention, there may be mentioned *Enterobacter aerogenes*, etc.

Moreover, as the bacterium of the genus *Ralstonia* usable in the third invention, there may be mentioned *Ralstonia eutropha*, etc.

Furthermore, as the bacterium of the genus *Actinobacillus* usable in the third invention, there may be mentioned *Actinobacillus succinogenes*, etc.

Still further, as the bacterium of the genus *Mannheimia* usable in the third invention, there may be mentioned *Mannheimia succiniciproducens*, etc.

Also, as the bacterium of the genus *Basfia* usable in the third invention, there may be mentioned *Basfia succiniciproducens*, etc. Further, as the bacterium of the genus *Zymomonas* usable in the third invention, there may be mentioned *Zymomonas mobilis*, etc. Moreover, as the bacterium of the genus *Zymobacter* usable in the third invention, there may be mentioned *Zymobacter palmae*, etc.

Also, as the filamentous fungus usable in the third invention, there may be mentioned the genus *Aspergillus*, the genus *Penicillium*, the genus *Rhizopus*, etc. Among these, as the genus *Aspergillus*, there may be mentioned *Aspergillus niger, Aspergillus oryzae*, etc., as the genus *Penicillium*, there may be mentioned *Penicillium chrysogenum, Penicillium simplicissimum*, etc. Further, as the genus *Rhizopus*, there may be mentioned *Rhizopus oryzae*, etc.

Also, as the yeast fungus usable in the third invention, there may be mentioned the genus *Saccharomyces*, the genus *Shizosaccharomyces*, the genus *Candida*, the genus *Pichia*, the genus *Kluyveromyces*, the genus *Yarrowia* and the genus *Zygosaccharomyces*.

As the above-mentioned genus *Saccharomyces*, there may be mentioned *Saccharomyces cerevisiae, Saccharomyces uvarum, Saccharomyces bayanus*, etc.

Also, as the above-mentioned genus *Shizosaccharomyces*, there may be mentioned *Schizosaccharomyces pombe*, etc.

Further, as the above-mentioned genus *Candida*, there may be mentioned *Candida albicans, Candida sonorensis, Candida glabrata*, etc. Moreover, as the above-mentioned *Pichia*, there may be mentioned *Pichia pastoris, Pichia stipitis*, etc.

Also, as the above-mentioned genus *Kluyveromyces*, there may be mentioned *Kluyveromyces lactis, Kluyveromyces marxianus, Kluyveromyces thermotolerans*, etc. Further, as the above-mentioned genus *Yarrowia*, there may be mentioned *Yarrowia lipolytica*, etc. Moreover, the above-mentioned genus *Zygosaccharomyces*, there may be mentioned *Zygosaccharomyces bailii, Zygosaccharomyces rouxii*, etc.

Among these, when succinic acid is to be produced as the above-mentioned useful substance, among the above-mentioned microorganisms, at least one selected from the group consisting of coryneform bacterium, *Escherichia coli*, a bacterium of the genus *Bacillus*, a bacterium of the genus *Klebsiella*, a bacterium of the genus *Serratia*, a bacterium of the genus *Clostridium*, a bacterium of the genus *Enterobacter*, a bacterium of the genus *Ralstonia*, a bacterium of the genus *Anaerobiospirillum*, a bacterium of the genus *Actinobacillus*, a bacterium of the genus *Mannheimia*, a bacterium of the genus *Basfia*, a bacterium of the genus *Zymobacter*, a filamentous fungus and a yeast fungus is preferred, more preferably coryneform bacterium, *Escherichia coli* or a yeast fungus, further preferably coryneform bacterium.

Also, when ethanol is to be produced as the above-mentioned useful substance, among the above-mentioned microorganisms, at least one selected from the group consisting of coryneform bacterium, *Escherichia coli*, a bacterium of the genus *Bacillus*, a bacterium of the genus *Klebsiella*, a bacterium of the genus *Serratia*, a bacterium of the genus *Clostridium*, a bacterium of the genus *Enterobacter*, a bacterium of the genus *Ralstonia*, a bacterium of the genus *Anaerobiospirillum*, a bacterium of the genus *Actinobacillus*, a bacterium of the genus *Mannheimia*, a bacterium of the genus *Basfia*, a bacterium of the genus *Zymomonas*, a bacterium of the genus *Zymobacter*, a filamentous fungus and a yeast fungus is preferred, more preferably coryneform bacterium, *Escherichia coli* or a yeast fungus, further preferably a yeast fungus.

Further, when butanediol, preferably 2,3-butanediol is to be produced as the above-mentioned useful substance, at least one selected from the group consisting of coryneform bacterium, *Escherichia coli*, a bacterium of the genus *Bacillus*, a bacterium of the genus *Klebsiella*, a bacterium of the genus *Serratia*, a bacterium of the genus *Clostridium*, a bacterium of the genus *Enterobacter*, a bacterium of the genus *Ralstonia*, a bacterium of the genus *Anaerobiospirillum*, a bacterium of the genus *Actinobacillus*, a bacterium of the genus *Mannheimia*, a bacterium of the genus *Basfia*, a bacterium of the genus *Zymomonas*, a bacterium of the genus *Zymobacter*, a filamentous fungus and a yeast fungus is preferred, more preferably coryneform bacterium, *Escherichia coli* or a yeast fungus, further preferably coryneform bacterium.

The above-mentioned microorganism may be any strain not only a wild strain, but also a mutant strain obtained by a general mutation treatment such as UV irradiation or NTG treatment, etc., a recombinant strain derived from a genetic means such as cell fusion and a gene recombination method, etc.

Also, the above-mentioned microorganism is a microorganism inherently having an ability of producing a useful substance, or may be a microorganism to which the useful substance-producing ability is provided by breeding.

As a means to provide the useful substance-producing ability by breeding, there may be mentioned a mutation treatment and a gene recombination treatment, etc., and conventionally known methods such as expression enhancement of enzyme gene in the useful substance biosynthetic pathway and expression reduction of enzyme gene in the by-product biosynthetic pathway may be employed. For example, when a carboxylic acid producing ability such as succinic acid, fumaric acid and malic acid, etc., is to be provided, there may be mentioned modification of reducing the lactate dehydrogenase activity mentioned later or a means to enhance the pyruvate carboxylase activity, etc. When an alcohol producing ability such as ethanol, butanol and butanediol, etc., is to be provided, there may be mentioned modification of reducing the lactate dehydrogenase activity mentioned later or a means to enhance the alcohol dehydrogenase activity, etc.

A modification method of reducing the above-mentioned lactate dehydrogenase (hereinafter referred to as LDH) activity is not particularly limited, the above-mentioned microorganism is used as a parental strain, treated by a mutation agent which has generally been used in the mutation treatment such as N-methyl-N'-nitro-N-nitrosoguanidine (NTG) and nitrous acid, etc., and a strain in which the LDH activity is reduced is selected. In addition, the microorganism may be modified by using a gene which encodes LDH. More specifically, it can be accomplished by the method in which an ldh gene on the chromosome is destroyed, or a method in which a promoter or an expression regulatory sequence such as Shine-Dalgarno (SD) sequence, etc., is modified, and the like.

As a specific preparation method of a strain in which an LDH activity is reduced, there may be mentioned a method by homologous recombination to the chromosome (see JP Hei. 11-206385A, etc.) or a method of using a sacB gene (Schafer A, Tauch A, Jager W, Kalinowski J, Thierbach G, Puhler A, Gene 1994 Vol. 145(1), pp. 69-73), etc.

A modification method of enhancing the above-mentioned pyruvate carboxylase (hereinafter also referred to as PC) activity is not particularly limited, the above-mentioned microorganism is used as a parental strain, treated by a mutation agent which has generally been used in the mutation treatment such as N-methyl-N'-nitro-N-nitrosoguanidine (NTG) and nitrous acid, etc., and a strain in which the PC activity is enhanced is selected. In addition, the microorganism may be modified by using a gene which encodes PC. More specifically, it can be accomplished by heightening a number of copies of the pc gene, and to heighten a number of copies can be accomplished by using a plasmid, or by making a multi-copying on the chromosome by the homologous recombination method, etc. Incidentally, enhancement of the PC activity can be also accomplished by highly expressing with introduction of mutation into the promoter of the pc gene on the chromosome or on the plasmid, or substitution with more potent promoter, etc.

The pc gene to be used for enhancement of the PC activity is not particularly limited as long as it encodes a protein having the PC activity and may be mentioned, for example, a gene derived from *Corynebacterium glutamicum*. Further, a pc gene derived from bacteria other than the coryneform bacterium, or other microorganisms or animals and plants may be also used. As the pc gene derived from the microorganism or animals and plants, a gene which encodes a protein having a PC activity is isolated from the chromosome of the microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

A PC expression vector can be provided by inserting the gene which encodes the PC isolated as mentioned above into the conventionally known expression vector. A PC activity-enhanced strain can be obtained by transforming with the expression vector. Or else, a PC activity-enhanced strain can be also obtained by expressably assembling a DNA which encodes the PC into a chromosome DNA of a host microorganism by homologous recombination, etc. Incidentally, transformation and homologous recombination can be carried out according to the general method known for a person skilled in the art.

When the PC gene is to be introduced on a chromosome or on a plasmid, a suitable promoter is assembled at a 5'-side upstream of the gene, more preferably a terminator is assembled at a 3'-side downstream, respectively. As the promoter and the terminator, these are not particularly limited as long as these have been known as a promoter and a terminator which acts in a microorganism utilizing as a host, which may be a promoter and a terminator of the pc gene itself, or may be substituted by the other promoters and terminators. These vectors, promoters and terminators, etc., which can be utilized in various kinds of microorganisms are described in detail in, for example, "Microbiology Basic Course 8 Genetic Engineering, published by Kyoritsu Shuppan Co., Ltd.", etc.

When an alcohol-producing ability is provided to the microorganism to be used in the present invention by breeding, a microorganism which has been modified so as to reduce an LDH activity may be utilized in the same manner as in the case where the carboxylic acid-producing ability is provided.

The microorganism which has been modified so as to enhance the above-mentioned alcohol dehydrogenase (hereinafter also referred to as ADH) activity can be produced by the same method of enhancing the PC activity as mentioned above.

The adh gene to be used for enhancing the ADH activity is not particularly limited as long as it encodes a protein having the ADH activity, and may be mentioned, for example, an adhB gene derived from *Zymomonas mobilis* and an adhE2 gene derived from *Clostridium acetobutylicum*. Further, an adh gene derived from bacteria other than those as mentioned above, or the other microorganisms or animals and plants may be also used. As the adh gene derived from the microorganism or animals and plants, a gene which encodes a protein having an ADH activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

Incidentally, the microorganism to be used in the present invention may be a microorganism obtained by two or more kinds of modifications among the modifications for providing the useful substance-producing ability. When a plural number of modifications are carried out, the order thereof is not limited.

The microorganism to be used in the third invention may be a microorganism having a useful substance-producing ability and having pentose utilizability, preferably a microorganism having pentose utilizability.

In the present invention, "pentose utilizability" means that the microorganism utilizes the pentose as a carbon source, and can proliferate or produce a useful substance.

The pentose in which the microorganism utilizes as a carbon source is not particularly limited as long as it can utilize as a carbon source. Specific examples thereof may be mentioned an aldopentose such as xylose, arabinose, ribose, lyxose, etc., a ketopentose such as ribulose, xylulose, etc.

Among these, an aldopentose is preferably used, and more preferably xylose and/or arabinose contained in a hemicellulose type biomass which is used as an inedible raw materials. Above all, particularly preferred is xylose which is contained in the hemicellulose type biomass with a large amount.

Here, the microorganism having a pentose utilizability may be a microorganism inherently having a pentose utilizability, or a pentose utilizability is provided by breeding.

As a means to provide a pentose utilizability by breeding, there may be mentioned the gene recombination treatment, etc., and a conventionally known method such as introduction of an enzyme gene of a pentose metabolic pathway, etc., may be employed. For example, when a xylose utilizability is to be provided, there may be mentioned a method in which a xylose isomerase gene is introduced as mentioned later, or a method in which a xylose reductase gene and a xylitol dehydrogenase gene are introduced, etc. When an arabinose utilizability is to be provided, there may be mentioned a method in which an arabinose isomerase gene and a ribulokinase gene and a ribulose 5-phosphate epimerase gene are introduced as mentioned later, etc.

In the following, as specific examples to provide a pentose utilizability by breeding, a modified example of providing a xylose utilizability and a modified example of providing an arabinose utilizability are explained.

The microorganism to which the xylose utilizability has been provided can be obtained by using the above-mentioned microorganism as a parental strain, and introducing a gene which encodes a protein having a xylose isomerase (hereinafter also referred to as XylA) activity to the parental strain.

Here, the "XylA activity" means an activity (EC: 5.3.1.5) which catalyzes the reaction of isomerizing the xylose to form a xylulose. Whether the XylA activity is provided or enhanced or not can be confirmed by measuring the XylA activity according to the conventionally known method, for example, the method of Gao, et. al., (Gao Q, Zhang M, McMillan J D, Kompala D S, Appl. Biochem. Biotechnol., 2002, Vol. 98 (100), pp. 341-55).

As a specific producing method of a strain to which the XylA activity has been provided or enhanced, it can be accomplished by the method in which the xylA gene is introduced by a plasmid, or a method in which it is introduced on a chromosome by the conventionally known homologous recombination method, etc.

The xylA gene to be used for conferment or enhancement of the XylA activity is not particularly limited as long as it encodes a protein having the XylA activity and may be mentioned, for example, a gene derived from *Escherichia coli*.

Further, a xylA gene derived from bacteria other than *Escherichia coli*, or the other microorganisms or animals and plants may be also used. As the xylA gene derived from the microorganism or animals and plants, a gene which encodes a protein having a XylA activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

A XylA expression vector can be provided by expressably inserting the gene which encodes the XylA isolated as mentioned above into the conventionally known expression vector. A strain to which the XylA activity has been provided or enhanced can be obtained by transforming with this expression vector. Or else, a XylA activity-provided or enhanced strain can be also obtained by expressably assembling a DNA which encodes the XylA into a chromosome DNA of a host microorganism by homologous recombination, etc. Incidentally, transformation and homologous recombination can be carried out according to the general method known for a person skilled in the art.

When the XylA gene is to be introduced on a chromosome or on a plasmid, a suitable promoter is assembled at a 5'-side upstream of the gene, more preferably a terminator is assembled at a 3'-side downstream, respectively. As the promoter and the terminator, these are not particularly limited as long as these have been known as a promoter and a terminator which acts in a microorganism utilizing as a host, which may be a promoter and a terminator of the xylA gene itself, or may be substituted by the other promoters and terminators. These vectors, promoters and terminators, etc., which can be utilized in various kinds of microorganisms are described in detail in, for example, "Microbiology Basic Course 8 Genetic Engineering, published by Kyoritsu Shuppan Co., Ltd.", etc.

Also, in conferment of the xylose utilizability, in addition to conferment or enhancement of the XylA activity, it may be a microorganism which has been modified to provide or enhance the xylulokinase (hereinafter also referred to as XylB) activity.

Here, the "XylB activity" means an activity (EC: 2.7.1.17) which catalyzes the reaction of phosphorylating the xylulose to form a xylulose 5 phosphoric acid. Whether the XylB activity is provided or enhanced or not can be confirmed by measuring the XylB activity according to the conventionally known method, for example, the method of Eliasson, et. al., (Eliasson A, Boles E, Johansson B, Otensterberg M, Thevelein J M, Spencer-Martins I, Juhnke H, Hahn-Hatengerdal B, Appl. Microbiol. Biotechnol., 2000, Vol. 53, pp. 376-82).

The strain to which the XylB activity is provided or enhanced can be produced in the same manner as in the method of providing or enhancing the XylA activity mentioned above.

As the xylB gene to be used for providing or enhancing the XylB activity, it is not particularly limited as long as it encodes a protein having the XylB activity and may be mentioned, for example, a gene derived from *Escherichia coli, Corynebacterium glutamicum*.

Further, a xylB gene derived from bacteria other than those as mentioned above, or the other microorganisms or animals and plants may be also used. As the xylB gene derived from the microorganism or animals and plants, a gene which encodes a protein having a XylB activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

When the XylA activity and the XylB activity is provided or enhanced, the xylA gene and the xylB gene to be introduced may exist on the same genetic locus, or each may exist on the different genetic locuses. Examples in which two genes exist on the same genetic locus, there may be mentioned, for example, an operon formed by linking the respective genes, etc.

The microorganism to which the xylose utilizability has been provided may be also obtained by using the above-mentioned microorganism as a parental strain, and introducing a gene which encodes a protein having the xylose reductase (hereinafter also referred to as XR) activity and a gene which encodes a protein having the xylitol dehydrogenase (hereinafter also referred to as XDH) activity into the parental strain.

Here, the "XR activity" means an activity (EC: 1.1.1.21) which catalyzes the reaction of reducing the xylose to form a xylitol. Whether the XR activity is provided or enhanced or not can be confirmed by measuring the XR activity according to the conventionally known method, for example, the method of Sasaki, et. al., (Sasaki M, Jojima T, Inui M, Yukawa H, Appl Microbiol Biotechnol., 2010, Vol. 86 (4), pp. 1057-66).

The strain to which the XR activity is provided or enhanced can be produced in the same manner as in the method of providing or enhancing the XylA activity mentioned above. As the xr gene to be used for providing or enhancing the XR activity, it is not particularly limited as long as it encodes a protein having the XR activity and may be mentioned, for example, a XYL1 gene derived from *Pichia stipitis*.

Further, an xr gene derived from the microorganism or animals and plants other than those mentioned above may be also used. As the xr gene derived from the microorganism or animals and plants, a gene which encodes a protein having a XR activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

Next, the "XDH activity" means an activity (EC: 1.1.1.9) which catalyzes the reaction of dehydrogenating the xylitol to form a xylulose. Whether the XDH activity is provided or enhanced or not can be confirmed by measuring the XDH activity according to the conventionally known method, for example, the method of Rizzi et. al., (Rizzi M, Harwart K, Erlemann P, Bui-Thahn N A, Dellweg H, J Ferment Bioeng., 1989, Vol. 67, pp. 20-24).

The strain to which the XDH activity is provided or enhanced can be produced in the same manner as in the method of providing or enhancing the XylA activity mentioned above. As the xdh gene to be used for providing or enhancing the XDH activity, it is not particularly limited as long as it encodes a protein having the XDH activity and may be mentioned, for example, an XYL2 gene derived from *Pichia stipitis*.

Further, an xdh gene derived from the microorganism or animals and plants other than those mentioned above may be also used. As the xdh gene derived from the microorganism or animals and plants, a gene which encodes a protein having a XDH activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

Also, in conferment of the xylose utilizability, in addition to conferment or enhancement of the XDH activity and the XR activity, it may be a microorganism which has been modified to provide or enhance the XylB activity. With regard to the conferment or enhancement of the XylB activity, it is as mentioned above. The microorganism to which the arabinose utilizability has been provided may be also obtained by using the above-mentioned microorganism as a parental strain, and introducing a gene which encodes a protein having the arabinose isomerase (hereinafter also referred to as AraA) activity, a gene which encodes a protein having the ribulokinase (hereinafter also referred to as AraB) activity and a gene which encodes a protein having the ribulose 5-phosphate epimerase (hereinafter also referred to as AraD) activity into the parental strain.

Here, the "AraA activity" means an activity (EC: 5.3.1.4) which catalyzes the reaction of isomerizing the arabinose to form a ribulose. Whether the AraA activity is provided or enhanced or not can be confirmed by measuring the AraA activity according to the conventionally known method, for example, the method of Patrick, et. al., (Patrick J W, Lee N, J. Biol. Chem., 1968, Vol. 243, pp. 4312-19).

The strain to which the AraA activity is provided or enhanced can be produced in the same manner as in the method of providing or enhancing the XylA activity mentioned above. As the araA gene to be used for providing or enhancing the AraA activity, it is not particularly limited as long as it encodes a protein having the AraA activity and may be mentioned, for example, a gene derived from *Escherichia coli* or *Corynebacterium glutamicum*.

Further, an araA gene derived from bacteria other than those as mentioned above, or the other microorganism or animals and plants may be also used. As the araA gene derived from the microorganism or animals and plants, a gene which encodes a protein having an AraA activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

Next, the "AraB activity" means an activity (EC: 2.7.1.16) which catalyzes the reaction of phosphorylating the ribulose to form a ribulose 5 phosphoric acid. Whether the AraB activity is provided or enhanced or not can be confirmed by measuring the AraB activity according to the conventionally known method, for example, the method of Lee, et. al., (Lee N, Englesberg E, Proc. Natl. Acad. Sci., 1962, Vol. 48, pp. 335-48).

The strain to which the AraB activity is provided or enhanced can be produced in the same manner as in the method of providing or enhancing the XylA activity mentioned above. As the araB gene to be used for providing or enhancing the AraB activity, it is not particularly limited as long as it encodes a protein having the AraB activity and may be mentioned, for example, a gene derived from *Escherichia coli* or *Corynebacterium glutamicum*.

Further, an araB gene derived from bacteria other than those as mentioned above, or the other microorganisms or animals and plants may be also used. As the araB gene derived from the microorganism or animals and plants, a gene which encodes a protein having an AraB activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

Further, the "AraD activity" means an activity (EC: 5.1.3.4) which catalyzes the reaction of isomerizing the ribulose 5 phosphoric acid to form a xylulose 5 phosphoric acid. Whether the AraD activity is provided or enhanced or not can be confirmed by measuring the AraD activity according to the conventionally known method, for example, the method of Deanda, et. al., (Deanda K, Zhang M, Eddy C, Picataggio S, Appl Environ Microbiol., 1996, Vol. 62(12), pp. 4465-70).

The strain to which the AraD activity is provided or enhanced can be produced in the same manner as in the method of providing or enhancing the XylA activity mentioned above. As the araD gene to be used for providing or enhancing the AraD activity, it is not particularly limited as long as it encodes a protein having the AraD activity and may be mentioned, for example, a gene derived from *Escherichia coli* or *Corynebacterium glutamicum*.

Further, an AraD gene derived from bacteria other than those as mentioned above, or the other microorganism, animals and plants may be also used. As the araD gene derived from the microorganism or animals and plants, a gene which encodes a protein having an AraD activity is isolated from the chromosome of a microorganism, animals and plants, etc., based on a gene, homology, etc., the base sequences of which have already been determined, and the base sequences of which is determined, etc., may be used. Also, after determination of the base sequence, a gene synthesized according to the sequence may be also used. These can be obtained by amplifying the promoter and the region containing the ORF portion by the hybridization method or the PCR method.

When the AraA activity, the AraB activity and the AraD activity are provided or enhanced, the araA gene, the araB gene and the araD gene to be introduced may exist on the same genetic locus, or each may exist on the different genetic locuses. Examples in which two or three genes exist on the same genetic locus, there may be mentioned, for example, an operon formed by linking the respective genes, etc.

Incidentally, the microorganism to be used in the third invention may be bacteria obtained by combining two or more modifications among the modifications for providing the pentose utilizability. When a plural number of the modifications are carried out, the order thereof is not limited.

Also, the microorganism to be used in the third invention may be a microorganism obtained by combining a modification to provide a useful substance-producing ability and a modification to provide pentose utilizability. When a plural number of the modifications are carried out, the order thereof is not limited.

An amount of the microbial cell of the microorganism to be used in the third invention is not particularly limited, and as a wet microbial cell mass based on the whole amount of the fermentation production liquid, generally 1 g/L or more, preferably 10 g/L or more, more preferably 20 g/L or more, and on the other hand, generally 700 g/L or less, preferably 500 g/L or less, further preferably 400 g/L or less.

(Aqueous Medium)

The aqueous medium to be used in the third invention means water, an aqueous solution comprising water as a main component, and a gel (agar), etc., an organic raw material containing a saccharide solution, a microorganism having a useful substance-producing ability, and an alcohol obtained by hydrogenating the carbonyl compound and/or the unsaturated alcohol other than the saccharide contained in an organic raw material, as well as a liquid containing a component(s) necessary for culture of the microorganism, which further contains a liquid or a solid which is not dissolved therein is dispersed.

The aqueous solution to be used in the aqueous medium used in the third invention may be mentioned, for example, a buffer such as a phosphate buffer, etc., and the gel may be mentioned, for example, a medium for culturing a microorganism, and the aqueous medium is preferably an aqueous solution containing a nitrogen source and an inorganic salt, etc. Here, the nitrogen source is not particularly limited as long as the microorganism used in the third invention can assimilate the nitrogen source to form an organic compound, more specifically, there may be mentioned various kinds of organic or inorganic nitrogen compounds such as an ammonium salt, a nitrate, urea, a soybean hydrolysate, casein decomposed product, peptone, yeast extract, meat extract, corn steep liquor, etc. The inorganic salt to be used may be mentioned various kinds of a phosphate, a sulfate, a metal salt of magnesium, potassium, manganese, iron, zinc, etc. Also, vitamins such as biotin, thiamine, pantothenic acid, inositol, nicotinic acid, etc., a factor which promotes growth such as a nucleotide, an amino acid, etc., may be added depending on necessity. Further, for the purpose of suppressing foaming at the time of the reaction, it is preferred to add a suitable amount of a commercially available defoaming agent to the aqueous medium.

Also, the aqueous medium may contain, for example, at least one selected from a carbonate ion, a bicarbonate ion and a carbon dioxide gas (a carbonic acid gas), in addition to the above-mentioned organic raw material, nitrogen source, inorganic salt, etc. The carbonate ion or the bicarbonate ion is supplied from magnesium carbonate, sodium carbonate, sodium bicarbonate, potassium carbonate, potassium bicarbonate, etc., which can be also used as a neutralizing agent, and may be supplied from carbonic acid or bicarbonic acid or a salt thereof, or a carbon dioxide gas depending on necessity. Specific examples of the salt of the carbonic acid or bicarbonic acid may be mentioned, for example, magnesium carbonate, ammonium carbonate, sodium carbonate, potassium carbonate, ammonium bicarbonate, sodium bicarbonate, potassium bicarbonate, etc.

A concentration of a carbonate ion or a bicarbonate ion to be contained in the aqueous medium is not particularly limited, and generally 1 mM or more, preferably 2 mM or more, further preferably 3 mM or more, and generally 500 mM or less, preferably 300 mM or less, more preferably 200 mM or less. When a carbon dioxide gas is to be contained, the carbon dioxide gas is preferably contained in an amount of generally 50 mg or more, preferably 100 mg or more, further preferably 150 mg or more per 1 L of the aqueous medium, and on the other hand, the carbon dioxide gas is preferably contained in an amount of generally 25 g or less, preferably 15 g or less, further preferably 10 g or less per 1 L of the aqueous medium.

A pH of the aqueous medium is preferably so adjusted to the range that the activity is most effectively shown, depending on the kind of the microorganism to be used. More specifically, when the coryneform bacterium is to be used, a pH of the aqueous medium is generally set to 5.5 or more, preferably 6 or more, more preferably 6.6 or more, further preferably 7.1 or more, and generally set to 10 or less, preferably 9.5 or less, more preferably 9.0 or less.

The pH of the aqueous medium can be adjusted, when the organic compound to be produced is an acidic substance, by adding sodium carbonate, sodium bicarbonate, potassium carbonate, potassium bicarbonate, magnesium carbonate, ammonium carbonate, ammonium bicarbonate, sodium hydroxide, calcium hydroxide, magnesium hydroxide, ammonia (ammonium hydroxide), or a mixture thereof, etc. When the organic compound to be produced is basic substance, it can be adjusted by adding an inorganic acid such as hydrochloric acid, sulfuric acid, phosphoric acid, etc., an organic acid such as acetic acid, etc., or a mixture thereof, etc., or feeding a carbon dioxide gas.

(Conditions of Process for Producing Organic Material)

A reaction time of the process for producing an organic material in the third invention is not particularly limited, generally 1 hour or longer, preferably 3 hours or longer, and generally 168 hours or shorter, preferably 72 hours or shorter.

The reaction temperature of the process for producing an organic material in the third invention may be carried out at the same temperature as the optimum growth temperature of the above-mentioned microorganism to be used, and it is advantageous to carry out at a temperature higher than the optimum growth temperature, generally at 2° C. or higher than the optimum growth temperature, preferably 7° C. or higher, more preferably 15° C. or higher, further preferably carry out at a temperature higher than 20° C. or more. More specifically, in the case of the coryneform bacterium, it is generally 35° C. or higher, preferably 37° C. or higher, further preferably 39° C. or higher, while it is generally 45° C. or lower, preferably 43° C. or lower, further preferably 41° C. or lower. During the organic compound producing reaction, it is not necessarily set usually within the range of 35° C. to 45° C., but it is desired to set within the above-mentioned temperature range with a time of 50% or more, preferably 80% or more of the whole reaction time.

The process for producing an organic material in the third invention may be carried out by passing a gas/air under stirring, which can be optionally selected depending on the characteristics of the organic material to be produced or the microbial cells, may be carried out in an aerobic atmosphere, or in an anaerobic atmosphere without passing a gas/air and no oxygen is fed. The state of "in an anaerobic atmosphere" herein mentioned can be obtained by the methods of, for example, reacting without passing a gas/air by closing the apparatus, reacting under feeding an inert gas such as a nitrogen gas, etc., or passing an inert gas containing a carbon dioxide gas, etc.

The process for producing an organic material in the third invention is not particularly limited, and can be applied to any of a batchwise reaction, a semi-batchwise reaction or a continuous reaction.

The third invention preferably has a process in which the above-mentioned microorganism is acted on an organic raw material containing a hydrogenated saccharide solution to form an organic compound, and recovering the same. A kind of the organic compound which can be produced and examples of the preferred organic compound are as mentioned above.

(Recovering Process and Purification Process of Organic Compound)

In the third invention, an organic compound is formed by the above-mentioned process for producing an organic material, and it can be accumulated in the aqueous medium. The organic compound accumulated in the above-mentioned process for producing an organic material may be recovered by a process of recovering the same from the aqueous medium according to the conventional method. More specifically, for example, when the accumulated organic compound is a carboxylic acid such as succinic acid, fumaric acid, malic acid, etc., it can be recovered by removing a solid material such as microbial cells by centrifugation, filtration, etc., then, desalting the same with an ion exchange resin, etc.

Also, in the third invention, it may further contain a process for purifying the material obtained in the recovering process as mentioned above. More specifically, the solution recovered from the aqueous medium reaction mixture is crystallized (crystallization) or purified through column chromatography to obtain a carboxylic acid.

When the accumulated organic compound is an alcohol such as ethanol, butanol, butanediol, etc., centrifugation, the alcohol can be purified by removing a solid material such as microbial cells, etc., by filtration, etc., then, condensed by distillation, etc., and the solution is subjected to membrane dehydration, etc.

For using the above-mentioned microorganism in the third invention, those subjected to slant culture at a solid medium such as an agar medium, etc., may be used directly, and if necessary, the above-mentioned microorganism provisionally cultured in a liquid medium may be used. That is, the above-mentioned microorganism is provisionally proliferated, and then, the organic compound may be produced by the above-mentioned microorganism. As mentioned above, by subjecting to a seed culture or a main culture, the above-mentioned microorganism can be provisionally proliferated, and as the organic raw material to be used at this time, the hydrogenated saccharide solution may be used, or the other organic raw materials may be used.

Incidentally, the organic compound may be produced while proliferating the microorganism subjected to seed culture or main culture in an aqueous medium, it is reacted with an organic raw material containing a hydrogenated saccharide solution, or the organic compound may be produced by reacting microbial cells proliferated by provisionally subjecting to seed culture or main culture with an organic raw material in an aqueous medium containing an organic raw material which contains the hydrogenated saccharide solution.

Also, the microorganism to be used in the third invention may be, in addition to the above-mentioned microorganism, a processed product of the microorganism can be used. The processed product of the microorganism may be mentioned, for example, fixed microbial cells in which the microbial cells of the microorganism have been fixed by acrylamide, carrageenan, etc., a crashed material in which microbial cells have been crushed, its centrifugation supernatant, or a fraction(s) in which the supernatant is partially purified by subjecting to the treatment with ammonium sulfate, etc.

<Fourth Invention: Culturing Method of Microorganism>

The culturing method of the fourth invention is to culture a microorganism having an ability of producing a useful substance using an organic raw material containing the hydrogenated saccharide solution of the present invention as a carbon source. The microorganism obtained by the culturing method of the present invention is, thereafter, acted on an organic raw material to produce an organic compound, and this can be recovered. As the organic raw material used at this time, the above-mentioned hydrogenated saccharide solution may be used, or the other organic raw material may be contained in the hydrogenated saccharide solution. A kind of the organic compound which can be produced and examples of the preferred organic compound are as mentioned below.

In the culturing method of the fourth invention, culture may be carried out at a solid medium such as an agar medium, etc., containing the hydrogenated saccharide solution, or may be carried out in a liquid medium containing the hydrogenated saccharide solution. By carrying out the seed culture or the main culture mentioned later, the above-mentioned microorganism to be supplied to the organic compound producing reaction can be proliferated.

The seed culture is to carry out for adjusting microbial cells of the above-mentioned microorganism to be supplied to the main culture. The medium to be used for the seed culture may be mentioned a usual medium which is used for culture of a microorganism, and preferably a medium containing a nitrogen source or an inorganic salt, etc. Here, the nitrogen source is not particularly limited as long as it is a nitrogen source that this microorganism can proliferate by assimilation, more specifically, there may be mentioned various kinds of organic or inorganic nitrogen compounds such as an ammonium salt, a nitrate, urea, a soybean hydrolysate, casein decomposed product, peptone, yeast extract, meat extract, corn steep liquor, etc. The inorganic salt to be used may be mentioned various kinds of phosphates, sulfates, metal salts of magnesium, potassium, manganese, iron, zinc, etc. Also, a vitamin such as biotin, thiamine, pantothenic acid, inositol and nicotinic acid, etc., and a factor which promotes growth such as a nucleotide, an amino acid, etc., may be added to the above, if necessary.

Further, if necessary, a hydrogenated saccharide solution may be added to the above-mentioned medium as a carbon source, or an organic raw material such as glucose, etc., may be added to the same.

The seed culture is preferably carried out under a general optimum growth temperature. The general optimum growth temperature means a temperature at which the growing rate is the fastest in the conditions to be used for production of the organic compound. Specific culture temperature is generally 25° C. to 40° C., and preferably 30° C. to 37° C. In the case of the coryneform bacterium, it is generally 25° C. to 35° C., more preferably 28° C. to 33° C., and particularly preferably about 30° C.

The seed culture is preferably carried out at a general optimum growth pH. The general growth optimum pH refers to a pH at which the growing rate is the fastest in the conditions to be used for production of the organic compound. Specific culture pH is generally a pH of 4 to 10, and preferably a pH of 6 to 8. In the case of the coryneform bacterium, it is generally a pH of 6 to 9, and preferably a pH of 6.5 to 8.5. Also, a culture time of the seed culture is not particularly limited as long as it is a time which can obtain a certain amount of the microbial cells, and generally 6 hours or longer and 96 hours or shorter. Further, in the seed culture of an aerobic microorganism, it is preferred to feed an oxygen by the method of passing air or stirring, etc.

The microbial cells after the seed culture can be used for a main culture mentioned later, and with regard to the seed culture, it may be omitted, and a material which has been subjected to slant culture at a solid medium such as an agar medium, etc., may be directly used for the main culture. Also, is necessary, the seed culture may be carried out repeatedly with several times.

The main culture is to be carried out for the purpose of preparing the above-mentioned microbial cells of the microorganism to be supplied to an organic compound producing reaction mentioned later, and an object thereof is mainly to increase an amount of the microbial cells. When the above-mentioned seed culture is carried out, the main culture is carried out by using the microbial cells obtained by the seed culture.

The medium to be used for the main culture may be mentioned a usual medium used for culture of the microorganism, and preferably a medium containing a nitrogen source and an inorganic salt, etc. Here, the nitrogen source is not particularly limited as long as it is a nitrogen source that this microorganism can proliferate by assimilation, more specifically, there may be mentioned various kinds of organic or inorganic nitrogen compounds such as an ammonium salt, a nitrate, urea, a soybean hydrolysate, a casein decomposed product, peptone, yeast extract, meat extract, corn steep liquor, etc. The inorganic salt to be used may be mentioned various kinds of a phosphate, a sulfate, a metal salt of magnesium, potassium, manganese, iron, zinc, etc. Also, vitamins such as biotin, thiamine, pantothenic acid, inositol, nicotinic acid, etc., a factor which promotes growth such as a nucleotide, an amino acid, etc., may be added depending on necessity. Further, for the purpose of suppressing foaming at the time of the reaction, it is preferred to add a suitable amount of a commercially available defoaming agent to the aqueous medium.

Also, in the main culture, an organic raw material containing the hydrogenated saccharide solution is used as a carbon source. The other organic raw materials may be added depending on necessity. The organic raw material other than the hydrogenated saccharide solution to be used in the main culture is not particularly limited as long as the above-mentioned microorganism can proliferate by assimilation, and generally used fermentable carbohydrates including a carbohydrate such as galactose, lactose, glucose, fructose, sucrose, saccharose, starch, cellulose, etc.; and a polyalcohol such as glycerol, mannitol, xylitol, ribitol, etc., and among these, glucose, sucrose or fructose is preferably used, and particularly preferably glucose or sucrose.

In addition, the main culture is preferably carried out at a general optimum growth temperature. Specific culture temperature is generally 25° C. to 40° C., and preferably 30° C. to 37° C. In the case of the coryneform bacterium, it is generally 25° C. to 35° C., more preferably 28° C. to 33° C., and particularly preferably about 30° C.

Also, the main culture is preferably carried out at a general optimum growth pH. Specific culture pH is generally a pH of 4 to 10, and preferably a pH of 6 to 8. In the case of the coryneform bacterium, it is generally a pH of 6 to 9, and preferably a pH of 6.5 to 8.5.

Also, a culture time of the main culture is not particularly limited as long as it is a time which can obtain a certain amount of the microbial cells, and generally 6 hours or longer and 96 hours or shorter. Further, in the main culture of an aerobic microorganism, it is preferred to feed an oxygen by the method of passing air or stirring, etc.

Moreover, in the main culture, as a producing method of the microbial cells more suitable for production of the organic compound, a method of carrying out the culture in which depletion and fulfillment of the carbon source are alternatively repeated with a short period of time as disclosed in JP 2008-259451A may be employed.

The microbial cell after the main culture can be used for an organic material producing reaction, and the culture liquid may be directly used or may be used after recovering the microbial cells by centrifugation, membrane separation, etc.

Also, a starch saccharified liquid, molasses, etc., containing the above-mentioned fermentable carbohydrates may be used, and the above-mentioned fermentable carbohydrates is preferably a saccharide solution squeezed from a plant such as saccharide cane, saccharide beets, saccharide maple, etc.

Further, the main culture is preferably carried out at a general optimum growth temperature. Specific culture temperature is generally 25° C. to 40° C., and preferably 30° C. to 37° C. In the case of the coryneform bacterium, it is generally 25° C. to 35° C., more preferably 28° C. to 33° C., and particularly preferably about 30° C.

Moreover, the main culture is preferably carried out at a general optimum growth pH. Specific culture pH is generally a pH of 4 to 10, and preferably a pH of 6 to 8. In the case of the coryneform bacterium, it is generally a pH of 6 to 9, and preferably a pH of 6.5 to 8.5.

Furthermore, a culture time of the main culture is not particularly limited as long as it is a time which can obtain a certain amount of the microbial cells, and generally 6 hours or longer and 96 hours or shorter. Also, in the main culture, it is preferred to feed an oxygen by the method of passing air or stirring, etc.

Moreover, in the main culture, as a producing method of the microbial cells more suitable for production of the organic compound, a method of carrying out the culture in which depletion and fulfillment of the carbon source are alternatively repeated with a short period of time as disclosed in JP 2008-259451A may be employed.

The microbial cell after the main culture can be used for the organic compound producing reaction mentioned later, and a culture liquid may be directly used, or may be used after recovering the microbial cell by centrifugation, membrane separation, etc.

EXAMPLES

In the following, the present invention is explained in more detail by referring to Examples, but the present invention is not limited by these Examples.

Analytical methods by GC and LC are shown below.
(Gas Chromatograph (GC) Analysis)
Apparatus: GC-2014 manufactured by Shimadzu Corporation
Column: J&W DB-1 60 m×0.25 mm, film thickness 0.25 μm manufactured by Agilent Technologies
Injection temperature: 230° C.
Detection temperature: 220° C.
Sprit ratio: 1/25
Gas flow amount: 1.5 mL/min
Temperature raising: maintained at 50° C. for 10 minutes, then, temperature raised to 220° C. with 15° C./min, and maintained at 220° C. for 8 minutes
(Liquid Phase Chromatograph (LC) Analysis)
Pump: LC-20AD manufactured by Shimadzu Corporation
Column oven: CTO-10A manufactured by Shimadzu Corporation
UV detector: SPD-10A manufactured by Shimadzu Corporation
RI detector: RID-10A manufactured by Shimadzu Corporation
Column: ULTRON PS-80H 8.0ID×300 mm manufactured by Shinwa Chemical Industries Ltd.
Apparatus: Eluent: 0.11% by mass perchloric acid solution 1.0 mL/min
Detection method: UV (210 nm), RI
Injection amount: 10 μL
(Measurement of Absorption Spectrum of Saccharide Solution)

Measurement apparatus: UV-1650PC manufactured by Shimadzu Corporation
Measurement temperature: 25° C.
Measurement cell: Quartz tube 10 mm
Dilution ratio: Object to be measured is diluted by ion-exchanged water Preparation of Saccharide Solution Preparation Example 1

In 90.7 mL of ultrapure water were dissolved 8.0 g of glucose, 1.0 g of xylose, 0.1 g of furfural, 0.04 g of formic acid and 0.3 g of glycolaldehyde dimer to prepare a saccharide solution. In the following, this is called as Saccharide solution-1.

When LC analysis of Saccharide solution-1 was carried out, it was 8.0% by mass of glucose, 1.0% by mass of xylose, 0.04% by mass of formic acid and 0.3% by mass of glycolaldehyde dimer.

Similarly, GC analysis of Saccharide solution-1 was carried out, it was 0.1% by mass of furfural.

Preparation Example 2

In 452 mL of ultrapure water were dissolved 40.1 g of glucose, 5.1 g of xylose, 0.5 g of furfural, 0.2 g of formic acid and 1.5 g of glycolaldehyde dimer to prepare a saccharide solution.

In a glass column was packed 3.6 mL of an anion exchange resin (available from Mitsubishi Chemical Corporation, porous type DIAION PA312LOH), among the saccharide solution passed through 99 g of the saccharide solution prepared as mentioned above, the first 5 mL was disposed, and the passed saccharide solution through the resin thereafter was recovered. The saccharide solution remained at the resin was washed with 5 mL of deionized water, and combined with the recovered saccharide solution (97.1 g). In the following, this is called as Saccharide solution-2.

Preparation Example 3

A saccharide solution (hereinafter referred to as Saccharide solution-0) in which 8.0 g of glucose and 1.0 g of xylose had been dissolved in 91.1 mL of ultrapure water was prepared. 12.0 g of Saccharide solution-1 prepared in Preparation example 1 and 3.0 g of the above-mentioned Saccharide solution-0 were mixed to prepare Saccharide solution-3 which contains 0.1% by mass of furfural, 0.03% by mass of formic acid and 0.2% by mass of glycolaldehyde dimer. An aldehyde content of Saccharide solution-3 corresponds to 0.8 equivalent of Saccharide solution-1.

Preparation Example 4

Similarly, 9.0 g of Saccharide solution-1 prepared in Preparation example 1 and 6.0 g of the above-mentioned Saccharide solution-0 were mixed to prepare Saccharide solution-4 which contains 0.06% by mass of furfural, 0.02% by mass of formic acid and 0.18% by mass of glycolaldehyde dimer. An aldehyde content of Saccharide solution-4 corresponds to 0.6 equivalent of Saccharide solution-1.

Preparation Example 5

Similarly, 6.0 g of Saccharide solution-1 prepared in Preparation example 1 and 9.0 g of the above-mentioned Saccharide solution-0 were mixed to prepare Saccharide solution-5 which contains 0.04% by mass of furfural, 0.02% by mass of formic acid and 0.1% by mass of glycolaldehyde dimer. An aldehyde content of Saccharide solution-5 corresponds to 0.4 equivalent of Saccharide solution-1.

Example 1

Hydrogenation Treatment of Saccharide Solution

To 70 mL of microautoclave was charged 0.1 g of 5% by mass Ru/C (available from N.E. Chemcat Corporation). To the material was added 20 g of Saccharide solution-1 prepared in Preparation example 1. After flowing argon into the reactor, the autoclave was closed. After replacing the inner system with 1 MPa of hydrogen four times, an airtightness test was carried out at an assumed maximum reaction pressure or more. After the airtightness test, the hydrogen was purged until the pressure became 0.9 MPa. An autoclave was placed in a reaction furnace a temperature of which was set to 60° C., the hydrogenation reaction was carried out for 1 hour, and the autoclave was taken out from the reaction furnace, and air-cooled. After cooling to 23° C., the content was taken out from the autoclave. The catalyst was filtered from the above-mentioned hydrogenation reaction liquid through a disposable syringe and a filter (0.45 µm) to obtain a hydrogenated Saccharide solution-1.

(Analysis of Hydrogenated Saccharide Solution-1)

When the hydrogenated Saccharide solution-1 was subjected to LC analysis as mentioned above, it contained 8.1% by mass of glucose, 1.1% by mass of xylose, 0.04% by mass of formic acid and 0.02% by mass of glycolaldehyde dimer. When GC analysis of the hydrogenated saccharide solution 1 was similarly carried out, then, furfural was the detection limit or less (less than 0.001% by mass), furfuryl alcohol was 0.01% by mass and tetrahydrofurfuryl alcohol was 0.06% by mass.

According to the hydrogenation reaction, furfural which is a fermentation inhibiting component was removed, and with regard to glycolaldehyde, the concentration thereof was markedly reduced.

Example 2

Hydrogenation Treatment of Saccharide Solution

The hydrogenation treatment was carried out in the same manner as in Example 1 except for using the above-mentioned Saccharide solution-2. When LC analysis of the saccharide solution (hereinafter referred to as hydrogenated Saccharide solution-2) subjected to the hydrogenation treatment was carried out, then, glucose was 7.8% by mass, xylose was 1.0% by mass, sorbitol was 0.05% by mass and xylitol was 0.04% by mass. No glycolaldehyde dimer was detected. When GC analysis of the saccharide solution subjected to the hydrogenation treatment was similarly carried out, then, furfural was the detection limit or less (less than 0.001% by mass), and tetrahydrofurfuryl alcohol was 0.09% by mass.

According to the hydrogenation reaction, furfural which is a fermentation inhibiting component was removed, and with regard to glycolaldehyde, the concentration thereof was markedly reduced.

Example 3

The hydrogenation treatment was carried out in the same manner as in Example 2 except for changing the reaction pressure at the time of the hydrogenation reaction to 0.4 MPa. When LC analysis of the saccharide solution (hereinafter referred to as hydrogenated Saccharide solution-3) subjected to the hydrogenation treatment was carried out, then, glucose was 7.8% by mass, xylose was 1.0% by mass, xylitol was 0.009% by mass and glycolaldehyde dimer was 0.005% by mass. When GC analysis of the saccharide solution subjected to the hydrogenation treatment was similarly carried out, then, furfural was the detection limit or less (less than 0.001% by mass), furfuryl alcohol was 0.006% by mass and tetrahydrofurfuryl alcohol was 0.05% by mass.

According to the hydrogenation reaction, furfural which is a fermentation inhibiting component was removed, and with regard to glycolaldehyde, the concentration thereof was markedly reduced.

Preparation Example 6

Preparation of Xylose Isomerase Gene and Xylulokinase Gene Introduced Strain

According to the method described in Example of the specification of JP Application No. 2013-161477, *Brevibacterium flavum* strain MJ233/XylAB/PC-4/ΔLDH was prepared from *Brevibacterium flavum* strain MJ233. Incidentally, in the following, the summary thereof is explained, and the contents of the above-mentioned specification are included in the present application by reference.

(A) Extraction of *Escherichia coli* Genome DNA

*Escherichia coli* (*Escherichia coli*) strain JM109 was cultured by 10 mL of a TB medium [47 g/L of Terrific Broth and 5 g/L of Glycerol] till the anaphase of the logarithmic growth phase, and gathered. The obtained microbial cell was suspended in 0.15 mL of a buffer [20 mM Tris-HCl pH 8.0, 10 mM NaCl, 1 mM EDTA 2Na] containing lysozyme with a concentration of 10 mg/mL. Next, to the above-mentioned suspension was added proteinase K so that the final concentration thereof became 100 µg/mL, and the mixture was maintained at 37° C. for 1 hour. Further, sodium lauryl sulfate was added so that the final concentration became 0.5%, and maintained the temperature at 50° C. for 6 hours to be subjected to bacteriolysis.

To the bacteriolyzed liquid was added an equal amount of a phenol/chloroform solution, and after gently shaking at room temperature for 10 minutes, the whole amount was centrifuged (5,000×g, 20 minutes, 10 to 12° C.), and the supernatant fraction was fractionated. Sodium acetate was added thereto so that it became 0.3M, then, 2-fold amount of ethanol was added thereto and mixed, a precipitate recovered by centrifugation (15,000×g, 2 minutes) was washed with 70% ethanol and air-dried. To the obtained DNA was added 5 mL of a TE buffer [10 mM Tris-HCl pH 7.5, 1 mM EDTA 2Na], allowed to stand at 4° C. overnight, and used as a template DNA in the subsequent PCR.

(B) Cloning of Xylose Isomerase-Xylulokinase Gene Operon

Acquisition of xylAB operon *Escherichia coli* strain JM109 was carried out by PCR using the DNA prepared in the above-mentioned (A) as a template, and using synthetic DNA: 5'-AAAGGATCCATCACCCGCGGCATTACCTG-3' (SEQ ID NO: 1) and 5'-TTTGGGCCCGTCGACTGAGATATATAGATGTGAATTATCC-3' (SEQ ID NO: 2) which have been designed based on the sequence (GenBank Accession No. U00096) at the peripheral of the operon of *Escherichia coli* strain K12-MG1655 the whole genome sequence of which have been reported.

1 µL of the template DNA, 0.5 µL of Pfx DNA polymerase (Invitrogen), 1-fold concentration of the buffer supplied by the manufacturer of the enzyme, 0.4 µM of each primer, 1 mM of $MgSO_4$ and 0.25 µM dNTPs were mixed, and the whole amount thereof was made 50 µL. The reaction temperature conditions are, by using a DNA thermal cycler PTC-200 (MJ Research), that a cycle comprising at 94° C. for 15 seconds, at 55° C. for 30 seconds, and at 68° C. for 3 minutes was repeated for 35 times. However, a temperature maintenance time at 94° C. of the first cycle was made 2 minutes and a temperature maintenance time at 68° C. of the final cycle was made 5 minutes.

Confirmation of the amplification product was carried out by separating with 0.9% agarose gel electrophoresis, and visualizing with ethidium bromide staining to detect a fragment of about 3.0 kb. The obtained DNA fragment of the xylAB operon was purified by using Charge Switch PCR Clean-Up Kit (Invitrogen), and then, cut by restriction enzymes BamHI and ApaI. The DNA fragment of about 2.9 kb formed by the above procedure was separated by 0.9% agarose gel electrophoresis, detected by visualizing with ethidium bromide staining, and recovered from a gel by using Zymoclean Gel DNA Recovery Kit (Zymo Research). This DNA fragment was mixed with the DNA prepared by cutting pTZ4 with restriction enzymes BamHI and ApaI, and ligated by using DNA Ligation Kit ver.2 (TAKARA BIO INC.). *Escherichia coli* (strain DH5α) was transformed by the obtained plasmid DNA, and smeared to LB agar medium containing 50 µg/mL of kanamycin. This clone grown on the medium was liquid cultured on a TB medium [47 g/L of Terrific Broth and 5 g/L of Glycerol] (containing 50 µg/mL of kanamycin), then, a plasmid DNA was prepared by using a QIAprep Spin Miniprep Kit (QIAGEN). When the thus obtained plasmid DNA was cut by restriction enzymes BamHI and ApaI, about 2.9 kb of inserted fragment was observed, which was named as pXylAB1.

(C) Extraction of *Brevibacterium flavum* Strain MJ233 Genomic DNA

*Brevibacterium flavum* strain MJ233 was cultured by 2% by mass glucose and 10 mL of a medium having the following composition [4 g of urea, 14 g of ammonium sulfate, 0.5 g of monopotassium phosphate, 0.5 g of dipotassium phosphate, 0.5 g of magnesium sulfate heptahydrate, 20 mg of ferrous sulfate heptahydrate, 20 mg of manganese sulfate pentahydrate, 200 µg of D-biotin, 200 µg of thiamine hydrochloride, 1 g of yeast extract and 1 g of casamino acid were dissolved in 1,000 mL of distilled water] (hereinafter referred to as medium (A)) till the anaphase of logarithmic growth phase, and gathered. The obtained microbial cells were suspended in 0.15 mL of a buffer [20 mM Tris-HCl pH=8.0, 10 mM NaCl, 1 mM EDTA 2Na] containing lysozyme with a concentration of 10 mg/mL To the obtained above-mentioned suspension was so added proteinase K that the final concentration thereof became 100 µg/mL, after maintaining at 37° C. for 1 hour, sodium lauryl sulfate was further so added thereto that the final concentration thereof became 0.5% by mass, and maintained at 50° C. for 6 hours to be subjected to bacteriolysis to prepare a bacteriolyzed liquid. To the above-mentioned bacteriolyzed liquid was added an equivalent amount of a phenol/chloroform solution, and after gently shaking at room temperature for 10 minutes, the whole amount was centrifuged (5,000×g, 20 minutes, 10 to 12° C.), and the supernatant fraction was fractionated.

To the above-mentioned supernatant fraction was so added sodium acetate that it became 0.3M, 2-fold amount of ethanol was added thereto and mixed, and a precipitate recovered by centrifugation (15,000×g, 2 minutes) was washed with 70% by volume of ethanol, and then, air-dried to obtain a DNA. To the obtained DNA was added 5 mL of a TE buffer [10 mM Tris-HCl pH 7.5, 1 mM EDTA 2Na], allowed to stand at 4° C. overnight, and used as a template DNA of the PCR at the later stage.

(D) Construction of Plasmid for Introducing Xylose Isomerase-Xylulokinase Gene Operon Cloning of the ldh gene was carried out to introduce *Escherichia coli* derived XylAB operon into a defective part of the ldh gene on a chromosome of *Brevibacterium flavum* strain MJ233/PC-4/ΔLDH (Specification of JP Application No. 2013-161477). Acquisition of the ldh gene of *Brevibacterium flavum* strain MJ233 was carried out by PCR using the DNA prepared in the above-mentioned (C) as a template, and using synthetic DNA: 5'-CGAGGGGTCGAGGAT-TCTGGGGAGGATCG AGTGGATTC-3' (SEQ ID NO: 3) and 5'-TCTAGAGTCGAGGATGGTGACCATGATGCAG-GATGGAG-3' (SEQ ID NO: 4) which have been designed based on the sequence (GenBank Accession No. BA000036) at the peripheral of the gene of *Corynebacterium glutamicum* strain ATCC13032 the whole genome sequences of which have been reported.

1 µL of the template DNA, 0.5 µL of Pfx DNA polymerase (Invitrogen), 1-fold concentration of the buffer supplied by the manufacturer of the enzyme, 0.4 µM of each primer, 1 mM $MgSO_4$ and 0.25 µM dNTPs were mixed, and the whole amount thereof was made 50 µL. The reaction temperature conditions are, by using a DNA thermal cycler PTC-200 (MJ Research), that a cycle comprising at 94° C. for 15 seconds, at 55° C. for 30 seconds, and at 68° C. for 2 minutes was repeated for 35 times. However, a temperature maintenance time at 94° C. of the first cycle was made 2 minutes and a temperature maintenance time at 68° C. of the final cycle was made 5 minutes.

Confirmation of the amplification product was carried out by separating with 0.9% agarose gel electrophoresis, and visualizing with ethidium bromide staining to detect a fragment of about 2.1 kb. The obtained DNA fragment of the ldh gene was purified by using Charge Switch PCR Clean-Up Kit (Invitrogen), bonded to XbaI portion of pKMB1 (JP 2005-95169A) using an In-Fusion Cloning Kit (TAKARA BIO INC.) and then, *Escherichia coli* strain DH5α was transformed by the obtained plasmid DNA. The thus obtained recombinant *Escherichia coli* was smeared to an LB agar medium containing 25 µg/mL of kanamycin and 25 µg/mL of X-Gal.

A clone which formed a white colony on the medium was liquid cultured by a TB medium [47 g/L of Terrific Broth and 5 g/L of Glycerol] (containing 25 µg/mL of kanamycin), and then, a plasmid DNA was formed by using a QIAprep Spin Miniprep Kit (QIAGEN). The thus obtained plasmid DNA was cut by restriction enzymes XhoI and BglI, and as a result, an inserted fragment with about 2.2 kb was confirmed, and this was named pKB-LDH2.

Acquisition of XylAB operon connected to a TZ4 promotor which is derived from *Brevibacterium flavum* strain MJ233 and constitutionary highly expressive was carried out by PCR using the plasmid pXylAB1 as a template, and using synthetic DNA: 5'-GTACCTGCAGGATGAGCGGGCT-3' (SEQ ID NO: 5) and 5'-CACCCGGTCAGGCAGGGGA-TAAC-3' (SEQ ID NO: 6).

1 µL of the template DNA, 0.5 µL of PrimeSTAR Max DNA polymerase (Invitrogen), 1-fold concentration attached buffer, 0.4 µM of each primer, 1 mM $MgSO_4$ and 0.25 µM dNTPs were mixed, and the whole amount thereof was made 50 µL. The reaction temperature conditions are, by using a DNA thermal cycler PTC-200 (MJ Research), that a cycle comprising at 94° C. for 15 seconds, at 55° C. for 20 seconds and at 72° C. for 45 seconds was repeated for 30 times. However, a temperature maintenance time at 94° C. of the first cycle was made 2 minutes.

Confirmation of the amplification product was carried out by separating with 0.7% agarose gel electrophoresis, and visualizing with ethidium bromide staining to detect a fragment of about 3.2 kb. The DNA fragment of the XylAB operon ligated to the TZ4 promoter was phosphated the 5'-end by T4 Polynucleotide Kinase (TAKARA BIO INC.), and then, ligated to EcoRV portion of pKB-LDH2 using a DNA Ligation Kit vert (TAKARA BIO INC.), and *Escherichia coli* strain DH5α was transformed by a plasmid DNA. The thus obtained recombinant *Escherichia coli* was smeared to an LB agar medium containing 25 µg/mL of kanamycin.

The clone grown on the medium was liquid cultured on a TB medium [47 g/L of Terrific Broth and 5 g/L of Glycerol] (containing 25 µg/mL of kanamycin), then by using a QIAprep Spin Miniprep Kit (QIAGEN), a plasmid DNA was prepared. The base sequence of the inserted fragment of the thus obtained plasmid DNA was determined by using a Big Dye Terminator v3 Cycle Sequencing Kit and a base sequence deciphering apparatus 377XL (Applied Biosystems). As a result, the obtained base sequence (XylAB operon) was completely matched with the genomic sequence of *Escherichia coli* strain K12-MG1655, and confirmed that no mutation was entered into the XylAB operon, which is named pXylAB3.

(E) Preparation of Xylose Isomerase-Xylulokinase Gene Operon Introduced Strain

The plasmid DNA to be used for transformation of the *Brevibacterium flavum* strain MJ233/PC-4/ΔLDH was prepared again from the *Escherichia coli* strain JM110 transformed by the calcium chloride method (Journal of Molecular Biology, 1970, 53, 159) using pXylAB3.

Transformation of the *Brevibacterium flavum* strain MJ233/PC-4/ΔLDH was carried out by the electric pulse method (Res. Microbiol., 1993, 144, p 181-5), and the obtained transformant was spread on an LBG agar medium [tryptone 10 g, yeast extract 5 g, NaCl 5 g, glucose 20 g and agar 15 g were dissolved in 1 L of distilled water] containing 25 µg/mL of kanamycin.

The strain grown on the medium is, since the pXylAB3 is a plasmid not replicable in the microbial cell of the *Brevibacterium flavum* strain MJ233, expected that a kanamycin resistant gene and a sacB gene derived from the plasmid would be inserted on the genome, as a result of causing homologous recombination between the ldh gene of the plasmid and the gene on the genome of the *Brevibacterium flavum* strain MJ233.

Next, the above-mentioned homologous recombination strain was liquid cultured in an LBG medium containing 25 µg/mL of kanamycin. The culture liquid corresponding to a number of the microbial cells of about 1,000,000 was smeared to an LBG medium containing 10% sucrose. As a result, several tens of strains which are considered to be sucrose insensitive by dropping the sacB gene according to the second homologous recombination.

Among the strains thus obtained, there are included a material in which an XylAB operon connected with a TZ4 promoter derived from pXylAB3 is inserted into the ldh gene defective site and a material which is returned to the same sequence as the parental strain. Whether the XylAB operon connected to the TZ4 promotor is inserted or not can be easily confirmed by applying the microbial cells obtained by culture in an LBG medium to the direct PCR reaction, and carrying out detection of the XylAB operon connected to the TZ4 promoter. When analysis is carried out using a primer: 5'-AATCAGGAAGTGGGATCGAAAATG-3' (SEQ ID NO: 7) and 5'-CCGCCAACTAGACAC-CAAAGATTC-3' (SEQ ID NO: 8) for PCR amplifying the TZ4 promoter and the XylAB operon, in the clone into which the XylAB operon connected with the TZ4 promoter has been inserted, 4,196 bp of a DNA fragment is to be recognized. When the strain which became sucrose insensitive was analyzed by the above-mentioned method, and as a result, strains into which the XylAB operon connected with the TZ4 promoter are selected, which strain was named as *Brevibacterium* flavum MJ233/XylAB/PC-4/ΔLDH.

(F) Xylose Assimilation Test

*Brevibacterium flavum* strain MJ233/XylAB/PC-4/ΔLDH prepared in the above-mentioned (E) was inoculated to an MM agar medium [2 g of urea, 7 g of $(NH_4)_2SO_4$, 0.5 g of $KH_2PO_4$, 0.5 g of $K_2HPO_4$, 0.5 g of $MgSO_4.7H_2O$, 6 mg of $FeSO_4.7H_2O$, 6 mg of $MnSO_4.4-5H_2O$, 200 ng of biotin, 200 µg of thiamine and 15 g of agar were dissolved in distilled water] containing 20 g/L of xylose, and allowed to stand and cultured at 30° C. for 3 days. As a comparison, *Brevibacterium flavum* strain MJ233/PC-4/ΔLDH was also similarly cultured. As a result, the *Brevibacterium flavum* strain MJ233/XylAB/PC-4/ΔLDH was confirmed to be grown in a medium which comprises xylose as a single carbon source. On the other hand, *Brevibacterium flavum* strain MJ233/PC-4/ΔLDH which is a parental strain could not be grown.

Example 4

Evaluation of Fermentation Production of Hydrogenated Saccharide Solution (A) Seed Culture 1,000 mL of the above-mentioned medium (A) was heat-sterilized at 121° C. for 20 minutes, cooled to room temperature, and then, 15 mL thereof was charged in 200 mL of a conical flask, and 600 µl of provisionally sterilized 50% glucose aqueous solution was added thereto. A strain *Brevibacterium flavum* MJ233/XylAB/PC-4/ΔLDH prepared in (E) of Preparation example 6 was inoculated and subjected to shaking culture at 30° C. for 5.1 hours.

(B) Main Culture

In 500 mL of a conical flask was charged 100 mL of the above-mentioned medium (A), and after adding 4 mL of previously sterilized 50% glucose aqueous solution thereto, the culture liquid obtained by seed culture of the above-mentioned (A) was inoculated so that O.D. (660 nm) became 0.05 and subjected to shaking culture at 30° C. for 19.4 hours.

(C) Succinic Acid Producing Reaction

The culture liquid obtained by the main culture in the above-mentioned (B) was gathered by 5,000×g for 7 minutes of centrifugation, and dispersed in a microbial cell suspension [1 g of magnesium sulfate heptahydrate, 40 mg of ferrous sulfate heptahydrate, 40 mg of manganese sulfate pentahydrate, 400 µg of D-biotin, 400 µg of thiamine chloride, 0.8 g of monoammonium phosphate, 0.8 g of diammonium phosphate and 1 g of potassium chloride were dissolved in 1,000 mL of distilled water] so that the O.D. (660 nm) became 20. Subsequently, 3 mL of the hydrogenated Saccharide solution-1 prepared in Example 1, 0.4 g of ammonium hydrogen carbonate and 3 mL of distilled water were mixed to prepare a substrate solution. In 5 mL of a reactor were mixed 0.5 mL of the above-mentioned microbial cell suspension and 0.5 mL of the substrate solution, and reacted at 40° C. under anaerobic conditions. As a result, a succinic acid accumulated concentration after 6 hours was 13.4 g/L, a glucose concentration was 0.1 g/L and a xylose concentration was 2.1 g/L.

Example 5

In the succinic acid producing reaction, the same procedures were carried out as in Example 4 except for using the hydrogenated Saccharide solution-2 prepared in Example 2. As a result, a succinic acid accumulated concentration after 6 hours was 12.6 g/L, a glucose concentration was 0.0 g/L and a xylose concentration was 1.7 g/L.

Example 6

In the succinic acid producing reaction, the same procedures were carried out as in Example 4 except for using the hydrogenated Saccharide solution-3 prepared in Example 3. As a result, a succinic acid accumulated concentration after 6 hours was 13.0 g/L, a glucose concentration was 0.1 g/L and a xylose concentration was 2.0 g/L.

Comparative Example 1

In the succinic acid producing reaction, the same procedures were carried out as in Example 4 except for using the Saccharide solution-1 prepared in Preparation example 1. As a result, a succinic acid accumulated concentration after 6 hours was 7.7 g/L, a glucose concentration was 8.3 g/L and a xylose concentration was 2.5 g/L.

Comparative Example 2

In the succinic acid producing reaction, the same procedures were carried out as in Example 4 except for using the Saccharide solution-3 prepared in Preparation example 3. As a result, a succinic acid accumulated concentration after 6 hours was 8.5 g/L, a glucose concentration was 6.7 g/L and a xylose concentration was 2.5 g/L.

Comparative Example 3

In the succinic acid producing reaction, the same procedures were carried out as in Example 4 except for using the Saccharide solution-4 prepared in Preparation example 4. As a result, a succinic acid accumulated concentration after 6 hours was 10.4 g/L, a glucose concentration was 3.4 g/L and a xylose concentration was 2.5 g/L.

Comparative Example 4

In the succinic acid producing reaction, the same procedures were carried out as in Example 4 except for using the Saccharide solution-5 prepared in Preparation example 5. As a result, a succinic acid accumulated concentration after 6 hours was 11.9 g/L, a glucose concentration was 1.3 g/L and a xylose concentration was 2.4 g/L.

Comparative Example 5

In the succinic acid producing reaction, the same procedures were carried out as in Example 4 except for using the Saccharide solution-0 prepared in Preparation example 3. As a result, a succinic acid accumulated concentration after 6 hours was 11.7 g/L, a glucose concentration was 2.2 g/L and a xylose concentration was 2.4 g/L.

The results of Examples 4 to 6 and Comparative examples 1 to 5 are shown in Table 1. The numerical values show concentrations of the respective components after 6 hours.

TABLE 1

|  | Kind of saccharide solution | Succinic acid concentration [g/L] | Glucose concentration [g/L] | Xylose concentration [g/L] |
| --- | --- | --- | --- | --- |
| Example 4 | Hydrogenation treated Saccharide solution-1 (Example 1) | 13.4 | 0.1 | 2.1 |
| Example 5 | Hydrogenation treated Saccharide solution-2 (Example 2) | 12.6 | 0 | 1.7 |
| Example 6 | Hydrogenation treated Saccharide solution-3 (Example 3) | 13 | 0.1 | 2 |
| Comparative example 1 | Saccharide solution-1 (Preparation example 1) | 7.7 | 8.3 | 2.5 |
| Comparative example 2 | Saccharide solution-3 (Preparation example 3) | 8.5 | 6.7 | 2.5 |
| Comparative example 3 | Saccharide solution-4 (Preparation example 4) | 10.4 | 3.4 | 2.5 |
| Comparative example 4 | Saccharide solution-5 (Preparation example 5) | 11.9 | 1.3 | 2.4 |
| Comparative example 5 | Saccharide solution-0 | 11.7 | 2.2 | 2.4 |

From Table 1, Example 4 which uses the hydrogenated Saccharide solution-1 of Example 1 is improved 74% in the succinic acid concentration as compared with that of Comparative example 1, improved 58% in the same as compared with that of Comparative example 2, improved 29% in the same as compared with that of Comparative example 3, improved 13% in the same as compared with that of Comparative example 4 and improved 15% in the same as compared with that of Comparative example 5.

From these results mentioned above, it can be clarified that a production rate of the succinic acid is improved by using a saccharide solution from which furfural, glycolaldehyde, etc., have been markedly removed by subjecting to the hydrogenation treatment.

From Table 1, Example 5 which uses the hydrogenated Saccharide solution-2 of Example 2 is improved 64% in the succinic acid concentration as compared with that of Comparative example 1, improved 48% in the same as compared with that of Comparative example 2, improved 21% in the same as compared with that of Comparative example 3, improved 6% in the same as compared with that of Comparative example 4 and improved 8% in the same as compared with that of Comparative example 5.

From these results mentioned above, it can be clarified that a production rate of the succinic acid is improved by using a saccharide solution from which furfural, glycolaldehyde, etc., have been markedly removed by subjecting to the hydrogenation treatment.

From Table 1, Example 6 which uses the hydrogenated Saccharide solution-3 of Example 3 is improved 69% in the succinic acid concentration as compared with that of Comparative example 1, improved 53% in the same as compared with that of Comparative example 2, improved 25% in the same as compared with that of Comparative example 3, improved 9% in the same as compared with that of Comparative example 4 and improved 11% in the same as compared with that of Comparative example 5.

From these results mentioned above, it can be clarified that a production rate of the succinic acid is improved by using a saccharide solution from which furfural, glycolaldehyde, etc., have been markedly removed by subjecting to the hydrogenation treatment.

From the above-mentioned results, it can be understood that by applying a saccharide solution containing a carbonyl compound and/or an unsaturated alcohol other than the saccharide to the hydrogenation reaction, the said substance(s) can be hydrogenated, and removed or markedly reduced. Further, it can be understood that by acting a microorganism on an organic raw material containing the obtained hydrogenated saccharide solution to produce an organic compound, a production rate of the organic compound is improved.

Example 7

The hydrogenation treatment was carried out in the same manner as in Example 1 by using the above-mentioned Saccharide solution-1. Concentrations of each component of the saccharide solution (hereinafter referred to as hydrogenated Saccharide solution-4) subjected to the hydrogenation treatment were, from the LC analysis by the above-mentioned conditions, 7.9% by mass of glucose, 1.0% by mass of xylose, 0.01% by mass of xylitol and sorbitol was the detection limit or less (less than 0.001% by mass). Neither glycolaldehyde dimer nor furfural was detected.

Example 8

The hydrogenation treatment was carried out in the same manner as in Example 1 except for using the above-mentioned Saccharide solution-1 and 5% by mass Pd/C (available from N.E. Chemcat Corporation) as a catalyst to obtain a hydrogenated saccharide solution (hereinafter referred to as hydrogenated Saccharide solution-5). Concentrations of each component of the hydrogenated Saccharide solution-5 were, from the LC analysis, 7.9% by mass of glucose, 1.0% by mass of xylose, 0.002% by mass of xylitol and sorbitol was the detection limit or less (less than 0.001% by mass). Also, glycolaldehyde dimer was 1,390 ppm and no furfural was detected.

Example 9

The succinic acid producing reaction was carried out in the same manner as in Example 4 through (A) the seed culture, (B) the main culture and (C) the succinic acid producing reaction except for using a substrate solution prepared by mixing 2.1 mL of the hydrogenated Saccharide solution-4 prepared in Example 7, 0.3 g of ammonium hydrogen carbonate and 2.9 mL of distilled water in place of using the hydrogenated Saccharide solution-1. As a result, a succinic acid accumulated concentration after 6 hours was 8.5 g/L, a glucose concentration was 3.2 g/L and a xylose concentration was 2.2 g/L.

Example 10

In the succinic acid producing reaction, the same procedures were carried out as in Example 9 except for using the hydrogenated Saccharide solution-5 prepared in Example 8. As a result, a succinic acid accumulated concentration after 6 hours was 7.7 g/L, a glucose concentration was 4.3 g/L and a xylose concentration was 2.4 g/L.

Comparative Example 6

In the succinic acid producing reaction, the same procedures were carried out as in Example 9 except for using the Saccharide solution-1 prepared in Preparation example 1. As a result, a succinic acid accumulated concentration after 6 hours was 6.4 g/L, a glucose concentration was 6.6 g/L and a xylose concentration was 2.0 g/L.

Comparative Example 7

In the succinic acid producing reaction, the same procedures were carried out as in Example 9 except for using the Saccharide solution-0 prepared in Preparation example 3. As a result, a succinic acid accumulated concentration after 6 hours was 8.5 g/L, a glucose concentration was 3.4 g/L and a xylose concentration was 2.4 g/L.

The results of Examples 9 and 10, and Comparative examples 6 and 7 are shown in Table 2. The numerical values show a concentration of each component after 6 hours.

TABLE 2

| | Kind of saccharide solution | Succinic acid concentration [g/L] | Glucose concentration [g/L] | Xylose concentration [g/L] |
| --- | --- | --- | --- | --- |
| Example 9 | Hydrogenation treated Saccharide solution-4 (Example 7) | 8.5 | 3.2 | 2.2 |
| Example 10 | Hydrogenation treated Saccharide solution-5 (Example 8) | 7.7 | 4.3 | 2.4 |
| Comparative example 6 | Saccharide solution-1 (Preparation example 1) | 6.4 | 6.6 | 2.0 |
| Comparative example 7 | Saccharide solution-0 (Preparation example 3) | 8.5 | 3.4 | 2.4 |

From Table 2, in Examples 9 and 10 using the hydrogenated Saccharide solutions-4 and 5, the succinic acid concentrations are improved 33% and 20%, respectively to that of Comparative example 6, and equal to that of Comparative example 7.

From the results mentioned above, even when the conditions of the hydrogenation treatment are different, by applying the carbonyl compound or the unsaturated alcohol to the hydrogenation reaction, it can be understood that these substances can be removed or markedly reduced. Further, it can be understood that by acting a microorganism on an organic raw material containing the obtained hydrogenated saccharide solution to produce an organic compound, a production rate of the organic compound is improved.

Example 11

The hydrogenation treatment was carried out in the same manner as in Example 1 except for using the above-mentioned Saccharide solution-1 and changing the reaction temperature to 90° C. to obtain a hydrogenated Saccharide solution-6. Concentrations of each component in the hydrogenated Saccharide solution-6 were 7.7% by mass of glucose, 0.8% by mass of xylose, 0.2% by mass of sorbitol, 0.2% by mass of xylitol, and neither glycolaldehyde dimer nor furfural was detected.

Example 12

The hydrogenation treatment was carried out in the same manner as in Example 1 except for using the above-mentioned Saccharide solution-1 and changing the reaction temperature to 120° C. to obtain a hydrogenated Saccharide solution-7. Concentrations of each component in the hydrogenated Saccharide solution-7 were 6.3% by mass of glucose, 0.5% by mass of xylose, 1.3% by mass of sorbitol, 0.6% by mass of xylitol and neither glycolaldehyde dimer nor furfural was detected.

Example 13

The hydrogenation treatment was carried out in the same manner as in Example 1 except for using the above-mentioned Saccharide solution-1 and changing the reaction temperature to 150° C. to obtain a hydrogenated Saccharide solution-8. Concentrations of each component in the hydrogenated Saccharide solution-8 were 5.5% by mass of glucose, 0.1% by mass of xylose, 2.5% by mass of sorbitol, 0.9% by mass of xylitol and neither glycolaldehyde dimer nor furfural was detected.

Example 14

The hydrogenation treatment was carried out in the same manner as in Example 8 except for using the above-mentioned Saccharide solution-1 and changing the reaction temperature to 90° C. to obtain a hydrogenated Saccharide solution-9. Concentrations of each component in the hydrogenated Saccharide solution-9 were 8.0% by mass of glucose, 1.0% by mass of xylose, a detection limit or less (less than 0.001% by mass) of sorbitol, 0.004% by mass of xylitol, 2,580 ppm of glycolaldehyde dimer and no furfural was detected.

Example 15

The hydrogenation treatment was carried out in the same manner as in Example 8 except for using the above-mentioned Saccharide solution-1 and changing the reaction temperature to 120° C. to obtain a hydrogenated Saccharide solution-10. Concentrations of each component in the hydrogenated Saccharide solution-10 were 7.9% by mass of glucose, 1.0% by mass of xylose, a detection limit or less (less than 0.001% by mass) of sorbitol, 0.014% by mass of xylitol, 1,820 ppm of glycolaldehyde dimer and no furfural was detected.

Example 16

The hydrogenation treatment was carried out in the same manner as in Example 8 except for using the above-mentioned Saccharide solution-1 and changing the reaction temperature to 150° C. to obtain a hydrogenated Saccharide solution-11. Concentrations of each component in the hydrogenated Saccharide solution-11 were 7.5% by mass of glucose, 1.0% by mass of xylose, 0.03% by mass of sorbitol, 0.07% by mass of xylitol, 2,310 ppm of glycolaldehyde dimer and no furfural was detected.

Example 17

The hydrogenation treatment was carried out in the same manner as in Example 1 except for using the above-mentioned Saccharide solution-1 and changing the reaction pressure to 3 MPa to obtain a hydrogenated Saccharide solution-12. Concentrations of each component in the hydrogenated Saccharide solution-12 were 7.8% by mass of glucose, 1.0% by mass of xylose, 0.01% by mass of xylitol and sorbitol was the detection limit or less (less than 0.001% by mass). Neither glycolaldehyde dimer nor furfural was detected.

Example 18

The hydrogenation treatment was carried out in the same manner as in Example 1 except for using the above-mentioned Saccharide solution-1 and changing the reaction pressure to 8 MPa to obtain a hydrogenated Saccharide solution-13. Concentrations of each component in the hydrogenated Saccharide solution-13 were 7.8% by mass of glucose, 0.9% by mass of xylose, 0.1% by mass of sorbitol and 0.1% by mass of xylitol. Neither glycolaldehyde dimer nor furfural was detected.

Example 19

In the succinic acid producing reaction, the same procedures were carried out as in Example 9 except for using the hydrogenated Saccharide solution-6 prepared in Example 11. As a result, a succinic acid accumulated concentration after 6 hours was 11.0 g/L, a glucose concentration was 0.42 g/L and a xylose concentration was 2.1 g/L.

Example 20

In the succinic acid producing reaction, the same procedures were carried out as in Example 9 except for using the hydrogenated Saccharide solution-7 prepared in Example 12. As a result, a succinic acid accumulated concentration after 6 hours was 8.5 g/L, a glucose concentration was 0.3 g/L and a xylose concentration was 0.3 g/L.

Example 21

In the succinic acid producing reaction, the same procedures were carried out as in Example 9 except for using the hydrogenated Saccharide solution-8 prepared in Example 13. As a result, a succinic acid accumulated concentration after 6 hours was 9.8 g/L, a glucose concentration was 0.3 g/L and a xylose concentration was 1.0 g/L.

Example 22

In the succinic acid producing reaction, the same procedures were carried out as in Example 9 except for using the hydrogenated Saccharide solution-9 prepared in Example 14. As a result, a succinic acid accumulated concentration after 6 hours was 8.6 g/L, a glucose concentration was 4.2 g/L and a xylose concentration was 1.8 g/L.

Example 23

In the succinic acid producing reaction, the same procedures were carried out as in Example 9 except for using the hydrogenated Saccharide solution-10 prepared in Example 15. As a result, a succinic acid accumulated concentration after 6 hours was 9.6 g/L, a glucose concentration was 2.5 g/L and a xylose concentration was 2.6 g/L.

Example 24

In the succinic acid producing reaction, the same procedures were carried out as in Example 9 except for using the hydrogenated Saccharide solution-11 prepared in Example 16. As a result, a succinic acid accumulated concentration after 6 hours was 9.4 g/L, a glucose concentration was 2.1 g/L and a xylose concentration was 2.6 g/L.

Example 25

In the succinic acid producing reaction, the same procedures were carried out as in Example 9 except for using the hydrogenated Saccharide solution-12 prepared in Example 17. As a result, a succinic acid accumulated concentration after 6 hours was 10.6 g/L, a glucose concentration was 1.6 g/L and a xylose concentration was 2.3 g/L.

Example 26

In the succinic acid producing reaction, the same procedures were carried out as in Example 9 except for using the hydrogenated Saccharide solution-13 prepared in Example 18. As a result, a succinic acid accumulated concentration after 6 hours was 10.9 g/L, a glucose concentration was 0.6 g/L and a xylose concentration was 2.4 g/L.

Comparative Example 8

In the succinic acid producing reaction, the same procedures were carried out as in Example 9 except for using the Saccharide solution-1 prepared in Preparation example 1. As a result, a succinic acid accumulated concentration after 6 hours was 7.5 g/L, a glucose concentration was 5.7 g/L and a xylose concentration was 2.5 g/L.

Comparative Example 9

In the succinic acid producing reaction, the same procedures were carried out as in Example 9 except for using the Saccharide solution-0 prepared in Preparation example 3. As a result, a succinic acid accumulated concentration after 6 hours was 10.7 g/L, a glucose concentration was 1.4 g/L and a xylose concentration was 2.5 g/L. The results of Examples 19 to 26, and Comparative examples 8 and 9 are shown in Table 3. The numerical values show concentrations of the respective components after 6 hours.

TABLE 3

| | Kind of saccharide solution | Succinic acid concentration [g/L] | Glucose concentration [g/L] | Xylose concentration [g/L] |
|---|---|---|---|---|
| Example 19 | Hydrogenation treated Saccharide solution-6 (Example 11) | 11.0 | 0.4 | 2.1 |
| Example 20 | Hydrogenation treated Saccharide solution-7 (Example 12) | 8.5 | 0.3 | 0.3 |
| Example 21 | Hydrogenation treated Saccharide solution-8 (Example 13) | 9.8 | 0.3 | 1.0 |
| Example 22 | Hydrogenation treated Saccharide solution-9 (Example 14) | 8.6 | 4.2 | 1.8 |
| Example 23 | Hydrogenation treated Saccharide solution-10 (Example 15) | 9.6 | 2.5 | 2.6 |
| Example 24 | Hydrogenation treated Saccharide solution-11 (Example 16) | 9.4 | 2.1 | 2.6 |
| Example 25 | Hydrogenation treated Saccharide solution-12 (Example 17) | 10.6 | 1.6 | 2.3 |
| Example 26 | Hydrogenation treated Saccharide solution-13 (Example 18) | 10.9 | 0.6 | 2.4 |
| Comparative example 8 | Saccharide solution-1 (Preparation example 1) | 7.5 | 5.7 | 2.5 |
| Comparative example 9 | Saccharide solution-0 (Preparation example 3) | 10.7 | 1.4 | 2.5 |

From Table 3, in Examples 19 to 26 using the hydrogenated Saccharide solutions-6 to 13, the succinic acid concentration is each improved as compared with that of Comparative example 8.

From the results mentioned above, even under the different hydrogenation treatment conditions in temperatures or reaction pressures, etc., it can be understood that a carbonyl compound or an unsaturated alcohol can be hydrogenated, and removed or markedly reduced. Further, it can be understood that by using the hydrogenated saccharide solution obtained under the different hydrogenation treatment conditions, a production rate of the organic compound is improved.

Preparation Example 7

In 181 mL of ultrapure water were dissolved 16.0 g of glucose, 2.0 g of xylose, 1.0 g of methyl acrylate and 0.08 g of formic acid to prepare a saccharide solution. It is hereinafter referred to as Saccharide solution-6.

Concentrations of each component in the Saccharide solution-6 were 8.0% by mass of glucose, 1.0% by mass of xylose, 0.04% by mass of formic acid and 0.5% by mass of methyl acrylate.

Example 27

The hydrogenation treatment was carried out in the same manner as in Example 1 except for using the above-mentioned Saccharide solution-6 to obtain a hydrogenated Saccharide solution-14. Concentrations of each component in the hydrogenated Saccharide solution-14 were 7.9% by mass of glucose, 1.0% by mass of xylose, a detection limit or less (less than 0.001% by mass) of sorbitol and 0.03% by mass of xylitol. No methyl acrylate was detected.

Example 28

In the succinic acid producing reaction, the same procedures were carried out as in Example 9 except for using the hydrogenated Saccharide solution-14 prepared in Example 27. As a result, a succinic acid accumulated concentration after 6 hours was 8.3 g/L, a glucose concentration was 3.7 g/L and a xylose concentration was 2.4 g/L.

Comparative Example 10

In the succinic acid producing reaction, the same procedures were carried out as in Example 9 except for using the Saccharide solution-6 prepared in Preparation example 7. As a result, a succinic acid accumulated concentration after 6 hours was 5.8 g/L, a glucose concentration was 8.0 g/L and a xylose concentration was 2.6 g/L.

Comparative Example 11

In the succinic acid producing reaction, the same procedures were carried out as in Example 9 except for using the Saccharide solution-0 prepared in Preparation example 3. As a result, a succinic acid accumulated concentration after 6 hours was 8.5 g/L, a glucose concentration was 3.4 g/L and a xylose concentration was 2.4 g/L.

The results of Example 28 and Comparative examples 10 and 11 are shown in Table 4. The numerical values show concentrations of the respective components after 6 hours.

TABLE 4

|  | Kind of saccharide solution | Succinic acid concentration [g/L] | Glucose concentration [g/L] | Xylose concentration [g/L] |
| --- | --- | --- | --- | --- |
| Example 28 | Hydrogenation treated Saccharide solution-14 (Example 27) | 8.3 | 3.7 | 2.4 |
| Comparative example 10 | Saccharide solution-6 (Preparation example 7) | 5.8 | 8.0 | 2.6 |
| Comparative example 11 | Saccharide solution-0 (Preparation example 3) | 8.5 | 3.4 | 2.4 |

From Table 4, in Example 28 using the hydrogenated Saccharide solution-14 of Example 27, the succinic acid concentration is improved 45% as compared with that of Comparative example 10.

From these results mentioned above, it can be clarified that a production rate of the succinic acid is improved by using a saccharide solution from which a methyl acrylate concentration which is an unsaturated ester compound is reduced, a production rate of the succinic acid is improved.

From the above, by applying a saccharide solution containing a carbonyl compound and/or an unsaturated alcohol other than the saccharide to the hydrogenation reaction, it can be understood that the said substance(s) can be hydrogenated, and removed or markedly reduced. Further, it can be understood that by acting a microorganism on an organic raw material containing the obtained hydrogenated saccharide solution to produce an organic compound, a production rate of the organic compound is improved.

Preparation Example 8

In 181 mL of ultrapure water were dissolved 16.0 g of glucose, 2.0 g of xylose, 1.0 g of crotyl alcohol and 0.08 g of formic acid to prepare a saccharide solution. This is hereinafter referred to as Saccharide solution-7.

Concentrations of each component in the above-mentioned Saccharide solution-7 were 7.9% by mass of glucose, 1.0% by mass of xylose, 0.04% by mass of formic acid and 0.5% by mass of crotyl alcohol.

Example 29

The hydrogenation treatment was carried out in the same manner as in Example 1 except for using the above-mentioned Saccharide solution-7 to obtain a hydrogenated Saccharide solution-15. Concentrations of each component in the hydrogenated Saccharide solution-15 were 7.9% by mass of glucose, 1.0% by mass of xylose, a detection limit or less (less than 0.001% by mass) of sorbitol and 0.013% by mass of xylitol. No crotyl alcohol was detected.

Example 30

In the succinic acid producing reaction, the same procedures were carried out as in Example 9 except for using the hydrogenated Saccharide solution-15 prepared in Example 29. As a result, a succinic acid accumulated concentration after 6 hours was 8.6 g/L, a glucose concentration was 3.0 g/L and a xylose concentration was 2.3 g/L.

Comparative Example 12

In the succinic acid producing reaction, the same procedures were carried out as in Example 9 except for using the Saccharide solution-7 prepared in Preparation example 8. As a result, a succinic acid accumulated concentration after 6 hours was 5.7 g/L, a glucose concentration was 7.3 g/L and a xylose concentration was 2.2 g/L.

Comparative Example 13

In the succinic acid producing reaction, the same procedures were carried out as in Example 9 except for using the Saccharide solution-0 prepared in Preparation example 3. As a result, a succinic acid accumulated concentration after 6 hours was 8.5 g/L, a glucose concentration was 3.4 g/L and a xylose concentration was 2.4 g/L.

Results of Example 30, and Comparative examples 12 and 13 are shown in Table 5. The numerical values show concentrations of the respective components after 6 hours.

TABLE 5

|  | Kind of saccharide solution | Succinic acid concentration [g/L] | Glucose concentration [g/L] | Xylose concentration [g/L] |
| --- | --- | --- | --- | --- |
| Example 30 | Hydrogenation treated Saccharide solution-15 (Example 29) | 8.6 | 3.0 | 2.3 |
| Comparative example 12 | Saccharide solution-7 (Preparation example 8) | 5.7 | 7.3 | 2.2 |
| Comparative example 13 | Saccharide solution-0 (Preparation example 3) | 8.5 | 3.4 | 2.4 |

From Table 5, in Example 30 using the hydrogenated Saccharide solution-15 of Example 29, the succinic acid concentration is improved 50% as compared with that of Comparative example 12.

From the results mentioned above, it can be clarified that a production rate of the succinic acid is improved by using a saccharide solution which has been subjected to hydrogenation treatment so that a concentration of crotyl alcohol which is the unsaturated alcohol is reduced.

From the results mentioned above, by applying the saccharide solution containing a carbonyl compound and/or an unsaturated alcohol other than the saccharide to the hydrogenation reaction, it can be understood that the said substance(s) is/are hydrogenated, and can be removed or markedly reduced. Further, it can be understood that by acting a microorganism on an organic raw material containing the obtained hydrogenated saccharide solution to produce an organic compound, a production rate of the organic compound is improved.

Comparative Example 14

By the above-mentioned Saccharide solution-1, 1% by mass activated charcoal MAXSORB (available from MC Evolve Technologies Corporation, MSP-20) was added to the total mass of the saccharides of glucose and xylose and the mixture was stirred at 25° C. for 2 hours. The above-mentioned reaction mixture was filtered by a disposable syringe and a filter (0.45 μm) to obtain an, activated charcoal-treated saccharide solution (in the following, "activated charcoal-treated Saccharide solution-1"). Concentrations of each component in the activated charcoal-treated Saccharide solution-1 were glucose 8.0% by mass, xylose 1.0% by mass, sorbitol 0.0% by mass and xylitol 0.0% by mass. Also, glycolaldehyde dimer was 3,200 ppm and furfural was 120 ppm.

Comparative Example 15

An activated charcoal-treatment was carried out in the same manner as in Comparative example 14 except for using the above-mentioned Saccharide solution-1, and changing the kind of the activated charcoal to DIASORB (available from Calgon Carbon Japan KK, W10-30) to obtain an activated charcoal-treated Saccharide solution-2. Concentrations of each component in the activated charcoal-treated Saccharide solution-2 were 8.00% by mass of glucose, 1.0% by mass of xylose, 0.0% by mass of sorbitol and 0.0% by mass of xylitol. Also, glycolaldehyde dimer was 3200 ppm and furfural was 120 ppm.

Comparative Example 16

In the succinic acid producing reaction, the same procedure was carried out as in Example 9 except for using the activated charcoal-treated Saccharide solution-1 prepared in Comparative example 14. As a result, the succinic acid accumulated concentration after 6 hours was 8.0 g/L, the glucose concentration was 8.0 g/L and the xylose concentration was 2.4 g/L.

Comparative Example 17

In the succinic acid producing reaction, the same procedure was carried out as in Example 9 except for using the activated charcoal-treated Saccharide solution-2 prepared in Comparative example 15. As a result, the succinic acid accumulated concentration after 6 hours was 7.5 g/L, the glucose concentration was 8.0 g/L and the xylose concentration was 2.3 g/L.

Comparative Example 18

In the succinic acid producing reaction, the same procedure was carried out as in Example 9 except for using Saccharide solution-1 prepared in Preparation example 1. As a result, the succinic acid accumulated concentration after 6 hours was 7.3 g/L, the glucose concentration was 9.6 g/L and the xylose concentration was 2.3 g/L.

Comparative Example 19

In the succinic acid producing reaction, the same procedure was carried out as in Example 9 except for using Saccharide solution-0 prepared in Preparation example 3. As a result, the succinic acid accumulated concentration after 6 hours was 12.0 g/L, the glucose concentration was 1.2 g/L and the xylose concentration was 1.9 g/L.

TABLE 6

|  | Kind of saccharide solution | Succinic acid concentration [g/L] | Glucose concentration [g/L] | Xylose concentration [g/L] |
|---|---|---|---|---|
| Comparative example 16 | Activated charcoal-treated saccharide solution-1 (Comparative example 14) | 8.0 | 8.0 | 2.4 |
| Comparative example 17 | ctivated charcoal-treated saccharide solution-2 (Comparative example 15) | 7.5 | 8.0 | 2.3 |
| Comparative example 18 | Saccharide solution-1 (Preparation example 1) | 7.3 | 9.6 | 2.3 |
| Comparative example 19 | Saccharide solution-0 (Preparation example 3) | 12.0 | 1.2 | 1.9 |

From Table 6, in Comparative example 16 using the activated charcoal-treated Saccharide solution-1, the succinic acid concentration was increased in 10% as compared with that of Comparative example 18. Also, in Comparative example 17 using the activated charcoal-treated Saccharide solution-2, the succinic acid concentration was increased in 3% as compared with that of Comparative example 18, but it is compared with the hydrogenation treatment, the recovery effect was a little.

From the results mentioned above, when the saccharide solution containing a carbonyl compound and/or an unsaturated alcohol is subjected to the activated charcoal-treatment, it can be understood that an effect of reducing the substance is a little as compared with the case where the saccharide solution has been subjected to the hydrogenation reaction. Further, when an organic compound is produced by acting a microorganism on the obtained activated charcoal-treated saccharide solution, it can be understood that improvement in the producing rate of the organic compound is a little.

Preparation Example 9

As the inedible raw materials, bagasse was used. First, to the bagasse were added sulfuric acid and water, and mixed to obtain a bagasse mixture. An amount of the sulfuric acid to be added is 2% by mass based on the dried mass of the bagasse, and an amount of the water was so adjusted that the water content based on the total mass of the above-mentioned bagasse mixture became 60% by mass. Next, the above-mentioned bagasse mixture was mixed and stirred by a drum mixer (manufactured by Sugiyama Heavy Industrial Co., Ltd.) for 20 minutes, and then, took out to obtain a dil. sulfuric acid treated mixture. The above-mentioned dil. sulfuric acid treated mixture was subjected to steaming treatment in a hydrolysis apparatus (manufactured by YASUJIMA Co., Ltd.) by introducing a vapor at 180° C. for 15 minutes. The water content of the obtained streamed material was 64.6% by mass. The above-mentioned steamed material was charged in a saccharifying apparatus so that the dried mass became 200 g/L, 10N—NaOH aqueous solution was added thereto to adjust a pH to 6.0. To the mixture was added 15 FPU of CTec2 (manufactured by Novozymes) as a saccharification enzyme, and hydrolysis was carried out at a temperature of 50° C., a stirring rate of 200 rpm for 72 hours under stirring. Thereafter, centrifugation (10,000 g, 10 minutes) was carried out to separate and remove undecomposed cellulose and lignin. To the saccharide solution from which the solid component has been removed, a pH thereof was adjusted to 8 by using 48% by mass NaOH aqueous solution, and further heated at 121° C. for 20 minutes to prepare a bagasse saccharified liquid (hereinafter referred to as Saccharide solution-8). The above-mentioned bagasse saccharified liquid was measured by the above-mentioned HPLC analysis, concentrations of each component therein were 9.0% by mass of glucose, 3.0% by mass in total of xylose and fructose, 816 ppm of furfural and 534 ppm of hydroxymethylfurfural.

Example 31

A hydrogenation treatment was carried out in the same manner as in Example 1 except for using the above-mentioned Saccharide solution-8 to obtain hydrogenated Saccharide solution-16. Concentrations of each component in the hydrogenated Saccharide solution-16 were 9.1% by mass of glucose, 3.0% by mass in total of xylose and fructose, and sorbitol and xylitol were the detection limits or less (less than 0.001% by mass). Also, furfural was 74 ppm and hydroxymethylfurfural was 126 ppm.

Example 32

A hydrogenation treatment was carried out in the same manner as in Example 8 except for using the above-mentioned Saccharide solution-8 to obtain a hydrogenated Saccharide solution-17. Concentrations of each component in the hydrogenated Saccharide solution-17 were 9.1% by mass of glucose, 3.0% by mass in total of xylose and fructose, 0.001% by mass of sorbitol and xylitol were the detection limits or less (less than 0.001% by mass). Also, furfural was 82 ppm and hydroxymethylfurfural was 130 ppm.

Example 33

A hydrogenation treatment was carried out in the same manner as in Example 15 except for using the above-mentioned Saccharide solution-8 to obtain a hydrogenated Saccharide solution-18. Concentrations of each component in the hydrogenated Saccharide solution-18 were 8.3% by mass of glucose, 3.3% by mass in total of xylose and fructose, 0.1% by mass of sorbitol and xylitol was the detection limit or less (less than 0.001% by mass) Also, furfural was 225 ppm and hydroxymethylfurfural was 228 ppm.

Example 34

A culture liquid obtained by the same processes of (A) seed culture and (B) the main culture in Example 4 was gathered in the same manner as in Example 4, and suspended in a microbial cell suspension [320 mg of magnesium sulfate heptahydrate, 13 mg of ferrous sulfate heptahydrate, 13 mg of manganese sulfate pentahydrate, 480 mg of phosphoric acid (85%) and 640 mg of potassium hydroxide (48%) were dissolved in 1,000 mL of distilled water] so that O.D. (660 nm) became 60 to prepare a microbial cell liquid. Subsequently, 54.5 g of the hydrogenated Saccharide solution-16 prepared in Example 31, 11 g of tilled water, and 1 mL of a medium concentrated liquid [25.6 g of magnesium sulfate heptahydrate, 1 g of ferrous sulfate heptahydrate, 1 g of manganese sulfate pentahydrate, 38.5 g of phosphoric acid (85%) and 50.9 g of potassium hydroxide (48%) are dissolved in 1,000 mL of distilled water], 133 mg of D-biotin aqueous solution (100 mg/L) and 133 mg of thiamine hydrochloride (100 mg/L) were mixed to prepare a substrate solution. To the substrate solution were added 960 mg of ammonium hydrogen carbonate and 20 mL of a microbial cell solution, and the mixture was reacted at 40° C. under an anaerobic atmosphere. By adding a neutralizing agent [117 g of aqueous ammonia (28%) and 38 g of ammonium hydrogen carbonate were dissolved in 300 mL of distilled water], a pH of the liquid was maintained to 7.3. As a result, a succinic acid accumulated concentration after 3 hours was 11.3 g/L.

Example 35

In the succinic acid producing reaction, the same procedures were carried out as in Example 34 except for using the hydrogenated Saccharide solution-17 prepared in Example 32. As a result, a succinic acid accumulated concentration after 3 hours was 11.7 g/L.

Example 36

In the succinic acid producing reaction, the same procedures were carried out as in Example 34 except for using the hydrogenated Saccharide solution-18 prepared in Example 33. As a result, a succinic acid accumulated concentration after 3 hours was 11.5 g/L.

Comparative Example 20

In the succinic acid producing reaction, the same procedures were carried out as in Example 34 except for the using Saccharide solution-8 prepared in Preparation example 9. As a result, a succinic acid accumulated concentration after 3 hours was 9.2 g/L.

The results of Examples 34 to 36 and Comparative example 20 are shown in Table 7. The reference numerals mean a succinic acid concentration after 3 hours.

Also, an absorption spectrum of the Saccharide solution-8 was measured by diluting the same with 75-fold (mass) of ion-exchanged water using a UV-vis measurement device with the same method as mentioned above, and the measured results were shown in FIG. 1

TABLE 7

| | Kind of saccharide solution | Succinic acid concentration [g/L] |
|---|---|---|
| Example 34 | Hydrogenation treated Saccharide solution-16 (Example 31) | 11.3 |
| Example 35 | Hydrogenation treated Saccharide solution-17 (Example 32) | 11.7 |
| Example 36 | Hydrogenation treated Saccharide solution-18 (Example 33) | 11.5 |
| Comparative example 20 | Saccharide solution-8 (Preparation example 9) | 9.2 |

From Table 7, in Examples 34 to 36 using the hydrogenated Saccharide solution-16 to 18, respectively, and the succinic acid concentrations to that of Comparative example 20 were each improved.

From the results mentioned above, the concentration(s) of a carbonyl compound and/or an unsaturated alcohol other than the saccharide contained in the saccharide solution can be markedly reduced by subjecting to the hydrogenation treatment to the bagasse saccharified liquid obtained from bagasse which is an inedible raw material. Further, it can be understood that by acting a microorganism on the hydrogenated saccharide solution derived from inedible raw materials to produce an organic compound, a production rate of the organic compound is improved.

Preparation Example 10

In 300 mL of ultrapure water were dissolved 98.6 g of glucose, 12.3 g of xylose, 0.3 g of furfural, 0.1 g of formic acid and 0.3 g of glycolaldehyde dimer to prepare a saccharide solution. In the following, this is called as Saccharide solution-9.

Concentrations of each component in the above-mentioned Saccharide solution-9 were 23.9% by mass of glucose, 3.0% by mass of xylose, 0.09% by mass of furfural, 0.03% by mass of formic acid and 0.08% by mass of glycolaldehyde dimer.

Preparation Example 11

In 300 mL of ultrapure water were dissolved 98.6 g of glucose, 12.3 g of xylose, 0.4 g of furfural, 0.16 g of formic acid and 0.41 g of glycolaldehyde dimer to prepare a saccharide solution. In the following, this is called as Saccharide solution-10.

Concentrations of each component in the Saccharide solution-10 were 23.9% by mass of glucose, 3.0% by mass of xylose, 0.12% by mass of furfural, 0.04% by mass of formic acid and 0.1% by mass of glycolaldehyde dimer.

Example 37

The hydrogenation treatment was carried out in the same manner as in Example 1 except for using the above-mentioned Saccharide solution-9 to obtain a hydrogenated Saccharide solution-19. Concentrations of each component in the hydrogenated Saccharide solution-19 were 23.8% by mass of glucose, 3.0% by mass of xylose, and sorbitol and xylitol were the detection limits or less (less than 0.001% by mass). Also, glycolaldehyde was 0.05% by mass and furfural was 0.0003% by mass.

Example 38

The hydrogenation treatment was carried out in the same manner as in Example 1 except for using the above-mentioned Saccharide solution-10 to obtain a hydrogenated Saccharide solution-20. Concentrations of each component in the hydrogenated Saccharide solution-20 were 23.7% by mass of glucose, 3.0% by mass of xylose and sorbitol and xylitol were the detection limit or less (less than 0.001% by mass), and neither glycolaldehyde dimer nor furfural was detected.

Preparation Example 12

With regard to Brevibacterium flavum strain MJ233, destruction of lactate dehydrogenase gene (ldh gene), phosphotransacetylase gene (pta gene), acetate kinase gene (ack gene), CoA transferase gene (ctf gene gene) and pyruvate oxidase gene (poxB gene), and further introduction of xylose isomerase gene (XylA gene), xylulokinase gene (XylB gene), acetolactate synthase gene (alsS gene), acetolactate carboxylase gene (alsD) and 2,3-butanediol dehydrogenase gene (bdhA gene) were carried out as mentioned below to prepare Brevibacterium flavum strain MJ233/BdhA/AlsSD/XylAB/ΔPoxB/ΔCTF/ΔPTA-ACK/ΔLDH.

<Preparation of XylAB Enhanced Strain>

As the strain to be tested for preparing an XylAB enhanced strain, Brevibacterium flavum strain MJ233/ΔPoxB/ΔCTF/ΔPTA-ACK/ΔLDH (JP Patent Application No. 2014-114971) was used. A plasmid DNA to be used for transformation of said strain was prepared from Escherichia coli strain JM110 transformed by the calcium chloride method (Journal of Molecular Biology, 1970, 53, 159) using the pXylAB3 which has been constructed in (C) of (Preparation example 6).

Transformation of Brevibacterium flavum Strain MJ233/ΔPoxB/ΔCTF/ΔPTA-ACK/ΔLDH was carried out by the electric pulse method (Res. Microbiol., 1993, 144, pp. 181-5), and the obtained transformant was smeared to an LBG agar medium [10 g of tryptone, 5 g of yeast extract, 5 g of NaCl, 20 g of glucose and 15 g of agar were dissolved in 1 L of distilled water] containing 25 μg/mL kanamycin.

Since the pXylAB3 is a plasmid nonduplicable in Brevibacterium flavum strain MJ233 microbial cell, as a result of causing homologous recombination between the ldh gene of the plasmid and the same gene on the Brevibacterium flavum strain MJ233 genome, a kanamycin resistance gene and a sacB gene derived from the said plasmid would be inserted onto the genome.

Next, the above-mentioned homologous recombination strain was liquid cultured in an LBG medium containing 25 μg/mL of kanamycin. As a result of smearing the microbial cells with a number of corresponding to about 1,000,000 of this culture liquid to an LBG medium containing 10% sucrose, several tens of strains which were considered to be sucrose insensitive by dropping the sacB gene were obtained at the second time homologous recombination.

Among the strains thus obtained, a strain in which the XylAB operon connected with the TZ4 promotor derived from pXylAB3 has been inserted on the ldh gene defective site and a strain which has been returned to the same sequence as those of the parental strain are contained. Whether the XylAB operon connected with the TZ4 promotor is inserted or not can be easily confirmed by applying microbial cells obtained by culturing in an LBG medium to the direct PCR reaction, and detection of the XylAB operon connected with the TZ4 promotor is carried out. When the TZ4 promotor and XylAB operon are analyzed by using a primer (SEQ ID NO: 9: AATCAGGAAG TGGGATCGAA AATG and SEQ ID NO: 10: CCGCCAACTA GACAC-CAAAG ATTC) for subjecting to the PCR amplification, a DNA fragment with 4,196 bp would be recognized in a clone into which the XylAB operon connected with the TZ4 promotor has been inserted. When the strains which became sucrose insensitive by the above-mentioned method were analyzed, and as a result, a strain to which the XylAB operon connected with the TZ4 promotor has been inserted was selected, which strain was named Brevibacterium flavum MJ233/XylAB/ΔPoxB/ΔCTF/ΔPTA-ACK/ΔLDH.

<Preparation of ALS, ALDC and BDH Enhanced Strain>

As the strain to be tested for preparing an alsSD and BdhA enhanced strain, Brevibacterium flavum strain MJ233/XylAB/ΔPoxB/ΔCTF/ΔPTA-ACK/ΔLDH prepared as mentioned above was used. A plasmid DNA to be used for transformation of said strain was prepared from Escherichia coli strain JM110 transformed according to the calcium chloride method (Journal of Molecular Biology, 1970, 53, 159) by using pC3.14F-AlsSD and pTZ4F-BdhA (JP Patent Application No. 2014-114971).

Transformation of the Brevibacterium flavum Strain MJ233/XylAB/ΔPoxB/ΔCTF/ΔPTA-ACK/ΔLDH was carried out by using the electric pulse method (Res. Microbiol., 1993, 144, pp. 181-5), and the obtained transformant was smeared to an LBG agar medium [10 g of tryptone, 5 g of yeast extract, 5 g of NaCl, 20 g of glucose and 15 g of agar were dissolved in 1 L of distilled water] containing 50 μg/mL of kanamycin and 10 μg/mL of streptomycin. In the strain grown on the medium, both of pC3.14F-AlsSD and pTZ4F-BdhA are retained in the *Brevibacterium flavum* strain MJ233 microbial cell, and this strain was named as *Brevibacterium flavum* MJ233/BdhA/AlsSD/ XylABLΔPoxB/ΔCTF/ΔPTA-ACK/ΔLDH (hereinafter also referred to as MBD07).

Example 39

(A) Seed Culture

To the solution containing the following components [ammonium sulfate: 20 g, urea: 5 g, monopotassium phosphate: 1 g, dipotassium phosphate: 1 g, manganese sulfate heptahydrate: 0.25 g and 3-morpholinopropanesulfonic acid: 42 g were dissolved in 600 mL of pure water] was added 1 mL of a calcium chloride solution [calcium chloride dihydrate: 1.32 g was dissolved in 100 mL of pure water], subsequently, it was adjusted to a pH of 7 with a 1N sodium hydroxide solution, and after making the liquid amount 864 mL by adding pure water, heat-sterilized at 121° C. for 20 minutes. Next, 1 mL of a filtration-sterilized trace element [to 1 g of ferrous sulfate heptahydrate, 1.42 g of manganese sulfate pentahydrate, 0.1 g of zinc sulfate heptahydrate, 0.031 g of sulfuric acid copper pentahydrate, 0.002 g of nickel chloride hexahydrate and 90 mL of pure water was added conc. Hydrochloric acid to adjust a pH=1], 1 mL of a filtration-sterilized protocatechuic acid solution [to 300 mg of protocatechuic acid and 8 mL of pure water was added 1 mL of 10N sodium hydroxide solution], 1 mL of a filtration-sterilized biotin solution [10 mg of D-biotin was dissolved in 50 mL of pure water] were added to prepare a medium.

In 200 mL of a conical flask were charged 17.3 mL of the above-mentioned medium, 1.1 mL of heat-sterilized pure water and 1.6 mL of 500 g/L heat-sterilized glucose solution to prepare a CGXII medium. Further, 20 μL of 50 g/L kanamycin solution and 20 μL of 25 g/L streptomycin solution were added thereto, and the strain MBD07 prepared in Preparation example 12 was inoculated and cultured at 30° C. for 24.0 hours.

(B) Production of 2,3-butanediol

In 200 mL of a conical flask, medium 43.3 mL of a sterilized medium was added to 6.7 mL of a filtration-sterilized hydrogenated Saccharide solution-19 which has been subjected to the hydrogenation reaction described in Example 37 to prepare a CGXII medium. Further, 50 μL of 50 g/L kanamycin solution and 50 μL of 25 g/L streptomycin solution were added to the same, a seed culture liquid was inoculated so that O.D. (660 nm) became 0.15, and cultured at 30° C. for 24.0 hours. O.D. (660 nm), glucose, xylose, (meso)-2,3-butanediol, (R,R) or (S,S)-2,3-butanediol and a total concentration (total of (meso), (R,R) and (S,S)) of 2,3-butanediol after 19.5 hours are shown in Table 8.

Comparative Example 21

In the production of 2,3-butanediol, the same procedure was carried out as in Example 39 except for using Saccharide solution-9. O.D. (660 nm), glucose, xylose, (meso)-2,3-butanediol, (R,R) or (S,S)-2,3-butanediol and the total concentration of 2,3-butanediol (total of (meso), (R,R) and (S,S)) after 19.5 hours are shown in Table 8.

Example 40

In the production of 2,3-butanediol, the same procedure was carried out as in Example 39 except for using the hydrogenated Saccharide solution-20 of Example 38. Glucose, xylose, (meso)-2,3-butanediol, (R,R) or (S,S)-2,3-butanediol and the total concentration of 2,3-butanediol (total of (meso), (R,R) and (S,S)) after 19.5 hours are shown in Table 8.

Comparative Example 22

In the production of 2,3-butanediol, the same procedure was carried out as in Example 39 except for using the Saccharide solution-10. Glucose, xylose, (meso)-2,3-butanediol, (R,R) or (S,S)-2,3-butanediol and the total concentration of 2,3-butanediol (total of (meso), (R,R) and (S,S)) after 19.5 hours are shown in Table 8.

Example 41

The hydrogenation treatment was carried out in the same method as in Example 1 except for using the above-mentioned Saccharide solution-8 to obtain a hydrogenated Saccharide solution-21. Concentrations of each component in the hydrogenated Saccharide solution-21 were 9.2% by mass of glucose, 2.9% by mass in total of xylose and fructose, 0.02% by mass of sorbitol, and xylitol was the detection limit or less (less than 0.001% by mass). Also, furfural was 172 ppm and hydroxymethylfurfural was 204 ppm. The hydrogenated Saccharide solution-21 was reduced in the degree of coloring by visual recognition with naked eyes as compared with that of Saccharide solution-8. In addition, the hydrogenated Saccharide solution-21 was diluted to 75-fold (mass) by ion-exchanged water, an absorption spectrum thereof was measured by a UV-vis measuring instrument, and the measured results were shown in FIG. 1.

Example 42

The hydrogenation treatment was carried out in the same manner as in Example 8 except for using the above-mentioned Saccharide solution-8 to obtain a hydrogenated Saccharide solution-22. Concentrations of each component in the hydrogenated Saccharide solution-22 were 9.1% by mass of glucose, 2.9% by mass in total of xylose and fructose, 0.003% by mass of sorbitol, and xylitol was the detection limit or less (less than 0.001% by mass). Also, furfural was 183 ppm and hydroxymethylfurfural was 219 ppm. The hydrogenated Saccharide solution-22 was reduced in the degree of coloring by visual recognition with naked eyes as compared with that of Saccharide solution-8. In addition, the hydrogenated Saccharide solution-22 was diluted to 75-fold (mass) by ion-exchanged water, an absorption spectrum thereof was measured by a UV-vis measuring instrument, and the measured results were shown in FIG. 1.

From FIG. 1, it can be understood that hydrogenated Saccharide solutions-21 and 22 are markedly reduced in the absorption at around 250 to 300 nm as compared with that of Saccharide solution-8 (Comparative example 20) before the hydrogenation treatment. It can be considered that the absorption region is mainly an absorption region of the carbonyl compound of the furfural, etc., so that the carbonyl compound is removed by the hydrogenation treatment whereby coloring is lowered. According to this procedure, the hydrogenated saccharide solution of the present invention is suppressed in coloring as compared with that before the treatment, so that it is applied to a reaction using the same, in particular, it is applied to a chemical conversion process, coloring of the product is considered to be suppressed.

Example 43

(A) Seed Culture

Seed culture was carried out in the same manner as in (A) seed culture of Example 39 except for changing an amount of the pure water to be used for dissolution to 330 mL and the liquid amount after adjusting to a pH=7 to 492 mL.

(B) Production of 2,3-butanediol

In 200 mL of a conical flask, 24.8 mL of a sterilized medium was added to 8.4 mL of heat-sterilized pure water and 16.8 mL of the hydrogenated Saccharide solution-21 obtained in Example 41 to prepare a CGXII medium. Further, 50 μL of 50 g/L kanamycin solution and 50 μL of 25 g/L streptomycin solution were added to the same, a seed culture liquid was inoculated so that O.D. (660 nm) became 0.20, and cultured at 30° C. for 24.0 hours. O.D. (660 nm), glucose, xylose, (meso)-2,3-butanediol, (R,R) or (S,S)-2,3-butanediol and a total concentration (total of (meso), (R,R) and (S,S)) of 2,3-butanediol after 19.0 hours are shown in Table 8.

Example 44

In the production of 2,3-butanediol, the same procedure was carried out as in Example 43 except for using the hydrogenated Saccharide solution-22 obtained in Example 42. O.D. (660 nm), glucose, xylose, (meso)-2,3-butanediol, (R,R) or (S,S)-2,3-butanediol and a total concentration (total of (meso), (R,R) and (S,S)) of 2,3-butanediol after 19.0 hours are shown in Table 8.

Comparative Example 23

In the production of 2,3-butanediol, the same procedure was carried out as in Example 43 except for using Saccharide solution-8. O.D. (660 nm), glucose, xylose, (meso)-2,3-butanediol, (R,R) or (S,S)-2,3-butanediol and a total concentration (total of (meso), (R,R) and (S,S)) of 2,3-butanediol are shown in Table 8.

Example 45

2,3-Butanediol was produced in the same manner as in Example 43 except for changing the amount of the above-mentioned hydrogenated Saccharide solution-21 to be used to 25.2 mL. The results are shown in Table 8.

Example 46

In the production of 2,3-butanediol, the same procedure was carried out as in Example 45 except for using the above-mentioned hydrogenated Saccharide solution-22. The results are shown in Table 8.

Comparative Example 24

In the production of 2,3-butanediol, the same procedure was carried out as in Example 45 except for using Saccharide solution-8. The results are shown in Table 8.

TABLE 8

| | Kind of saccharide solution | O.D. (660 nm) | Glucose concentration [g/L] | Xylose concentration [g/L] | Acetoin concentration [g/L] | 2,3-Butanediol concentration*[1] [g/L] |
|---|---|---|---|---|---|---|
| Example 39 | Hydrogenation treated Saccharide solution-19 | 18.0 | 10.3 | 4.2 | 0.9 | 0.1 (meso isomer) 4.6 (optical isomer) 4.7 (total) |
| Example 40 | Hydrogenation treated Saccharide solution-20 | 19.1 | 10.4 | 4.2 | 1.0 | 0.1 4.6 4.7 |
| Example 43 | Hydrogenation treated Saccharide solution-21 | 15.9 | 13.2 | 6.8 | 0.6 | 0.1 5.9 6.0 |
| Example 44 | Hydrogenation treated Saccharide solution-22 | 14.9 | 14.2 | 6.7 | 0.5 | 0.1 5.3 5.4 |
| Example 45 | Hydrogenation treated Saccharide solution-21 | 11.4 | 35.7 | 10.5 | 0.5 | 0.1 4.2 4.3 |
| Example 46 | Hydrogenation treated Saccharide solution-22 | 10.9 | 36.6 | 11.1 | 0.5 | 0.0 3.8 3.8 |
| Comparative example 21 | Saccharide solution-9 | 13.9 | 16.4 | 4.2 | 0.8 | 0.0 4.1 4.1 |

TABLE 8-continued

|  | Kind of saccharide solution | O.D. (660 nm) | Glucose concentration [g/L] | Xylose concentration [g/L] | Acetoin concentration [g/L] | 2,3-Butanediol concentration*[1] [g/L] |
|---|---|---|---|---|---|---|
| Comparative example 22 | Saccharide solution-10 | 11.3 | 21.0 | 4.3 | 0.7 | 0.0<br>3.5<br>3.6 |
| Comparative example 23 | Saccharide solution-8 | 9.9 | 21.2 | 6.9 | 0.6 | 0.0<br>3.5<br>3.5 |
| Comparative example 24 | Saccharide solution-8 | 3.3 | 45.3 | 14.4 | 1.0 | 0.0<br>0.4<br>0.4 |

*[1] 2,3-Butanediol concentration shows the respective amounts of a meso isomer, an optical isomer ((R,R)- or (S,S)-isomer) and a total amount thereof in this order.

From Table 8, when the hydrogenated Saccharide solution-19 of Example 39 was used, as compared with Saccharide solution-9 which has not been subjected to the hydrogenation treatment of Comparative example 21, O.D. (660 nm) was improved 1.3-fold and 2,3-butanediol concentrations (total of (meso), (R,R) and (S,S)) were improved 1.1-fold.

Also, when the hydrogenated Saccharide solution-20 of Example 40 was used, as compared with Saccharide solution-10 which has not been subjected to the hydrogenation treatment of Comparative example 22, O.D. (660 nm) was improved 1.7-fold and 2,3-butanediol concentrations (total of (meso), (R,R) and (S,S)) were improved 1.3-fold.

From the results mentioned above, by using the saccharide solution in which furfural, glycolaldehyde, etc., have been markedly reduced by subjecting to the hydrogenation treatment, it could be clarified that the proliferation rate of the microbial cell and the production rate of 2,3-butanediol were improved.

Further, when the hydrogenated Saccharide solution-21 of Example 43 was used, as compared with Saccharide solution-8 which has not been subjected to the hydrogenation treatment of Comparative example 23, O.D. (660 nm) was improved 1.6-fold and 2,3-butanediol concentrations (total of (meso), (R,R) and (S,S)) were improved 1.7-fold, and similarly when the hydrogenated Saccharide solution-22 of Example 44 was used, as compared with Saccharide solution-8 which has not been subjected to the hydrogenation treatment of Comparative example 23, O.D. (660 nm) was improved 1.5-fold and 2,3-butanediol concentrations (total of (meso), (R,R) and (S,S)) were improved 1.5-fold.

Moreover, when the hydrogenated Saccharide solution-21 of Example 45 was used, as compared with Saccharide solution-8 which has not been subjected to the hydrogenation treatment of Comparative example 24, O.D. (660 nm) was improved 3.5-fold and 2,3-butanediol concentrations (total of (meso), (R,R) and (S,S)) were improved 10.8-fold, similarly when the hydrogenated Saccharide solution-22 of Example 46 was used, as compared with Saccharide solution-8 which has not been subjected to the hydrogenation treatment of Comparative example 24, O.D. (660 nm) was improved 3.3-fold and 2,3-butanediol concentrations (total of (meso), (R,R) and (S,S)) were improved 9.5-fold.

From the results mentioned above, it can be clarified when the saccharide solution containing the carbonyl compound and/or the unsaturated alcohol other than the saccharide is subjected to hydrogenation treatment and a microorganism is acted on the obtained hydrogenated saccharide solution, the production rate of 2,3-butanediol is improved. Further, it can be clarified that the hydrogenated saccharide solution improves the proliferation rate of the microbial cells.

According to the above, it can be understood that by subjecting the saccharide solution to the hydrogenation reaction, a microorganism is acted on the hydrogenated saccharide solution in which said substances are removed or markedly reduced by hydrogenation to produce an organic compound, whereby the production rate of the organic compound can be improved. Further, it can be understood that the hydrogenated saccharide solution improves the culture rate of the microorganism. It can be understood that this effect is the same in the case where a bagasse saccharified liquid derived from inedible raw materials is subjected to hydrogenation treatment, and a microorganism is acted on the obtained hydrogenated saccharide solution.

Example 47

The hydrogenation treatment was carried out in the same manner as in Example 1 using the above-mentioned Saccharide solution-1 to obtain a hydrogenated Saccharide solution-23. Concentrations of each component in the hydrogenated Saccharide solution-23 were 8.0% by mass of glucose, 1.0% by mass of xylose, 0.01% by mass of xylitol, and sorbitol was the detection limit or less (less than 0.001% by mass). Also, glycolaldehyde dimer was 50 ppm and furfural was not detected.

Example 48

(A) Seed Culture 500 mL of a medium [20 g of polypeptone, 10 g of yeast extract were dissolved in 500 mL of pure water] was charged in a reagent bottle, and heat-sterilized at 121° C. for 20 minutes. This was cooled to room temperature, 10 mL thereof was charged in 200 mL of a conical flask, subsequently, 0.8 mL of 500 g/L heat-sterilized glucose aqueous solution and 9.2 mL of heat-sterilized pure water were charged therein to prepare a YPD medium. Next, *Saccharomyces cerevisiae* strain S288C was inoculated and cultured at 30° C. for 16.5 hours.

(B) Production of Ethanol

To 200 mL of a conical flask were added 10 mL of a heat-sterilized medium, 6.7 mL of the hydrogenated Saccharide solution-23 described in Example 47 (hydrogenation treatment of the saccharide solution) which has been filtration-sterilized through a filter having a pore size of 0.22 μm and 3.3 mL of heat-sterilized desalted water, and a pH thereof was adjusted to 6.3 with a filtration-sterilized NaOH solution. Next, the seed culture liquid was so inoculated that O.D. (660 nm) became 0.4, and cultured at 30° C. for 24.0 hours. An ethanol concentration, a glucose concentration and a xylose concentration after 9 hours are shown in Table 9.

Comparative Example 25

In the Production of Ethanol, the Same Procedure was Carried Out as in Example 48 except for using the saccharide solution-1 without subjecting to the hydrogenation treatment. O.D. (660 nm), glucose, xylose and ethanol concentrations after 9 hours are shown in Table 9.

TABLE 9

| | Kind of saccharide solution | O.D. (660 nm) | Glucose concentration [g/L] | Xylose concentration [g/L] | Ethanol concentration [g/L] |
| --- | --- | --- | --- | --- | --- |
| Example 48 | Hydrogenation treated Saccharide solution-23 | 13.3 | 5.4 | 3.6 | 8.7 |
| Comparative example 25 | Saccharide solution-1 | 2.8 | 21.4 | 3.8 | 2.5 |

From Table 9, when the hydrogenated Saccharide solution-23 of Example 47 was used, O.D. (660 nm) was improved 4.8-fold and the ethanol concentration 3.5-fold as compared with those of Saccharide solution-1 which has not been subjected to the hydrogenation treatment of Comparative example 25.

From the results mentioned above, it can be clarified when the saccharide solution containing the carbonyl compound and/or the unsaturated alcohol other than the saccharide is subjected to hydrogenation treatment and a microorganism is acted on the obtained hydrogenated saccharide solution, the production rate of ethanol is improved. Further, it can be clarified that the hydrogenated saccharide solution improves the proliferation rate of the microbial cells.

According to the above, it can be understood that by subjecting the saccharide solution to the hydrogenation reaction, a microorganism is acted on the hydrogenated saccharide solution in which said substances are removed or markedly reduced by hydrogenation to produce an organic compound, whereby the production rate of the organic compound can be improved. Further, it can be understood that the hydrogenated saccharide solution improves the culture rate of the microorganism.

Example 49

(A) Seed Culture 500 mL of a medium [3.0 g of monopotassium phosphate, 7.0 g of dipotassium phosphate, 2.0 g of ammonium sulfate, 0.2 g of magnesium sulfate heptahydrate, 10.0 g of sodium chloride, 5.0 g of yeast extract and 10.0 g of tryptone were dissolved in 500 mL of pure water] was charged in a reagent bottle, and heat-sterilized at 121° C. for 20 minutes. This was cooled to room temperature, 10 mL thereof was charged in 200 mL of a conical flask, subsequently, 0.8 mL of 500 g/L heat-sterilized glucose aqueous solution and 9.2 mL of heat-sterilized pure water were charged therein. Next, *Escherichia coli* strain K12 was inoculated and subjected to shaking culture at 30° C. for 16.5 hours.

(B) Main Culture

In 200 mL of a conical flask were charged 10 mL of the above-mentioned heat-sterilized medium, 2.2 mL of the filtration-sterilized hydrogenated Saccharide solution-23 described in Example 47, 0.36 mL of 500 g/L heat-sterilized glucose solution, 0.22 mL of 100 g/L heat-sterilized xylose solution, 7.2 mL of heat-sterilized pure water and 25 µL of 1N filtration-sterilized sodium hydroxide solution. Next, the culture liquid obtained in (A) seed culture mentioned above was inoculated so that O.D. (660 nm) became 0.1, and subjected to shaking culture at 30° C. for 24.0 hours. O.D. (660 nm), and glucose and xylose concentrations after 3.0 hours are shown in Table 10.

Comparative Example 26

In the microorganism culture, the same procedure as in Example 49 was carried out except for using Saccharide solution-1. O.D. (660 nm), and glucose and xylose concentrations after 3.0 hours are shown in Table 10.

Example 50

In 200 mL of a conical flask were charged 10 mL of the above-mentioned heat-sterilized medium, 4.5 mL of the hydrogenated Saccharide solution-23 described in Example 47, 5.5 mL of heat-sterilized pure water and 50 µL of 1N filtration-sterilized sodium hydroxide solution. Next, the culture liquid obtained in (A) seed culture obtained as mentioned above was inoculated so that O.D. (660 nm) became 0.1, and subjected to shaking culture at 30° C. for 24.0 hours. O.D. (660 nm), and glucose and xylose concentrations after 3.0 hours are shown in Table 10.

Comparative Example 27

In the microorganism culture, the same procedure as in Example 50 was carried out except for using Saccharide solution-1. O.D. (660 nm), and glucose and xylose concentrations after 3.0 hours are shown in Table 10.

TABLE 10

| | Kind of saccharide solution | O.D. (660 nm) | Glucose concentration [g/L] | Xylose concentration [g/L] |
| --- | --- | --- | --- | --- |
| Example 49 | Hydrogenation treated Saccharide solution-23 | 4.8 | 14.4 | 1.3 |
| Example 50 | Hydrogenation treated Saccharide solution-23 | 4.5 | 13.5 | 2.3 |
| Comparative example 26 | Saccharide solution-1 | 0.5 | 14.4 | 2.3 |
| Comparative example 27 | Saccharide solution-1 | 0.1 | 22.1 | 2.5 |

From Table 10, in Example 49, when the hydrogenated Saccharide solution-23 of Example 47 is used, O.D. (660 nm) is improved 9.6-fold as compared to the case where Saccharide solution-1 which has not been subjected to the hydrogenation treatment of Comparative example 26.

Also, in Example 50, when the hydrogenated Saccharide solution-23 is used, O.D. (660 nm) is improved 45.0-fold as compared to the case where Saccharide solution-1 which has not been subjected to the hydrogenation treatment of Comparative example 27.

From the results mentioned above, it can be clarified when the saccharide solution containing the carbonyl compound and/or the unsaturated alcohol other than the saccharide is subjected to hydrogenation treatment and a microorganism is acted on the obtained hydrogenated saccharide solution, the proliferation rate of microbial cells is improved. Further, it can be clarified that the hydrogenated saccharide solution improves the proliferation rate of the microbial cells.

According to the above, it can be confirmed that by subjecting the said saccharide solution to the hydrogenation reaction, the hydrogenated saccharide solution in which the said substances are removed or markedly reduced improves the culture rate of the microorganism.

Example 51

The hydrogenation treatment was carried out in the same manner as in Example 1 using the above-mentioned Saccharide solution-1. To the saccharide solution subjected to the hydrogenation treatment was adjusted a pH to 8 with 48% NaOH aqueous solution and the mixture was subjected to sterilization treatment by heating to 121° C. for 20 minutes. When the LC analysis was carried out about this saccharide solution, then, a glucose concentration was 7.78% by mass.

Comparative Example 28

By using 105.2 g of the above-mentioned Saccharide solution-1, 0.9 g (1 equivalent based on the total amount of the aldehyde) of sodium sulfite was added thereto, and the mixture was stirred at 40° C. for 1 hour. To the saccharide solution treated by a reducing agent was adjusted to a pH to 8 with 48% NaOH aqueous solution and the mixture was subjected to sterilization treatment by heating to 121° C. for 20 minutes. When the LC analysis was carried out about this saccharide solution, then, a glucose concentration was 4.7% by mass.

It can be clarified that the saccharide solution treated by the reducing agent is poor in heat stability and a glucose concentration thereof is markedly lowered, while the saccharide solution which has been subjected to the hydrogenation treatment has high heat stability and can maintain a glucose concentration constant.

UTILIZABILITY IN INDUSTRY

According to the treatment method of the saccharide of the present invention, a content of the fermentation inhibitor in the saccharide solution can be reduced, so that the obtainable saccharide solution is used in the fermentation production process utilizing the microorganism, an objective organic compound can be obtained with high yield.

Also, the hydrogenated saccharide solution of the present invention can improve production efficiency of the microorganism in producing the organic compound according to the fermentation production, and suppress coloring of the organic compound which is the product when it is utilized for the chemical conversion process.

Further, the method for producing an organic compound of the present invention can give a desired organic compound with a relatively simple and easy treatment and high production efficiency.

Moreover, when the culturing method of the present invention is employed, an amount of a fermentation inhibitor in the fermentation production process can be reduced so that it can improve the growth yield and the proliferation rate of the microorganism, whereby fermentation productivity can be improved.

SEQUENCE LISTING sequence

---

The invention claimed is:

1. A method for producing an organic compound, the method comprising:

hydrogenating a saccharide solution which comprises saccharide and at least one selected from the group consisting of a carbonyl compound and an unsaturated alcohol at a temperature of 120° C. or less, wherein the carbonyl compound is other than a saccharide, and producing an organic material in which a microorganism capable of producing an organic material is acted in an aqueous medium on an organic raw material containing the saccharide solution, and in which the microorganism contacts the hydrogenated saccharide solution, after the hydrogenating of the saccharide solution.

2. The method for producing an organic compound according to claim 1, wherein the producing of the organic material is carried out under an anaerobic atmosphere.

3. The method for producing an organic compound according to claim 1, further comprising purifying the organic compound obtained in the producing of the organic material.

4. The method for producing an organic compound according to claim 1, wherein the aqueous medium comprises at least one selected from a carbonate ion, a bicarbonate ion, and a carbon dioxide gas.

5. The method for producing an organic compound according to claim 1, wherein the organic compound is at least one selected from an alcohol, an amine, a carboxylic acid and a phenol.

6. The method for producing an organic compound according to claim 5, wherein the alcohol is an aliphatic alcohol having 2 to 10 carbon atoms.

7. The method for producing an organic compound according to claim 5, wherein the carboxylic acid is an aliphatic carboxylic acid having 2 to 10 carbon atoms.

8. The method according to claim 1, wherein the microorganism is at least one selected from the group consisting of coryneform bacterium, *Escherichia coli*, a bacterium of the genus *Anaerobiospirillum*, a bacterium of the genus *Actinobacillus*, a bacterium of the genus *Mannheimia*, a bacterium of the genus *Basfia*, a bacterium of the genus *Zymomonas*, a bacterium of the genus *Zymobacter*, a fungus and a yeast.

9. The method according to claim 1, wherein the microorganism can utilize pentose nutritionally.

10. The method according to claim 9, wherein the pentose is xylose.

11. The method according to claim 10, wherein the microorganism is a microorganism in which a xylose isomerase activity is provided or enhanced by introducing a gene which encodes a protein having a xylose isomerase activity to a parental strain of the microorganism.

12. The method according to claim 11, wherein the microorganism is a microorganism in which a xylulokinase activity is provided or enhanced by introducing a gene which encodes a protein having xylulokinase activity to a parental strain of the microorganism.

13. The method for producing an organic compound according to claim 1, wherein the hydrogenation of the saccharide solution is carried out at a temperature from 20 to 120° C.

* * * * *

SEQUENCE LISTING

```
<160> NUMBER OF SEQ ID NOS: 10

<210> SEQ ID NO 1
<211> LENGTH: 29
<212> TYPE: DNA
<213> ORGANISM: Artificial Sequence
<220> FEATURE:
<223> OTHER INFORMATION: Synthetic primer

<400> SEQUENCE: 1
aaaggatcca tcacccgcgg cattacctg                                    29

<210> SEQ ID NO 2
<211> LENGTH: 40
<212> TYPE: DNA
<213> ORGANISM: Artificial Sequence
<220> FEATURE:
<223> OTHER INFORMATION: Synthetic primer

<400> SEQUENCE: 2
tttgggcccg tcgactgaga tatatagatg tgaattatcc                        40

<210> SEQ ID NO 3
<211> LENGTH: 38
<212> TYPE: DNA
<213> ORGANISM: Artificial Sequence
<220> FEATURE:
<223> OTHER INFORMATION: Synthetic primer

<400> SEQUENCE: 3
```
cgaggggtcg aggattctgg ggaggatcga gtggattc          38

<210> SEQ ID NO 4
<211> LENGTH: 38
<212> TYPE: DNA
<213> ORGANISM: Artificial Sequence
<220> FEATURE:
<223> OTHER INFORMATION: Synthetic primer

<400> SEQUENCE: 4
tctagagtcg aggatggtga ccatgatgca ggatggag          38

<210> SEQ ID NO 5
<211> LENGTH: 22
<212> TYPE: DNA
<213> ORGANISM: Artificial Sequence
<220> FEATURE:
<223> OTHER INFORMATION: Synthetic primer

<400> SEQUENCE: 5
gtacctgcag gatgagcggg ct          22

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
cacccggtca ggcagggat aac          23

<210> SEQ ID NO 7
<211> LENGTH: 24
<212> TYPE: DNA
<213> ORGANISM: Artificial Sequence
<220> FEATURE:
<223> OTHER INFORMATION: Synthetic primer

<400> SEQUENCE: 7
aatcaggaag tgggatcgaa aatg          24

<210> SEQ ID NO 8
<211> LENGTH: 24
<212> TYPE: DNA
<213> ORGANISM: Artificial Sequence
<220> FEATURE:
<223> OTHER INFORMATION: Synthetic primer

<400> SEQUENCE: 8
ccgccaacta gacaccaaag attc          24

<210> SEQ ID NO 9
<211> LENGTH: 24
<212> TYPE: DNA
<213> ORGANISM: Artificial Sequence
<220> FEATURE:
<223> OTHER INFORMATION: Synthetic primer

<400> SEQUENCE: 9
aatcaggaag tgggatcgaa aatg          24

<210> SEQ ID NO 10
<211> LENGTH: 24
<212> TYPE: DNA
<213> ORGANISM: Artificial Sequence

```
<220> FEATURE:
<223> OTHER INFORMATION: Synthetic primer

<400> SEQUENCE: 10
ccgccaacta gacaccaaag attc                                          24
```